(12) United States Patent
Dunkel et al.

(10) Patent No.: US 7,820,708 B2
(45) Date of Patent: Oct. 26, 2010

(54) CARBOXAMIDES

(75) Inventors: Ralf Dunkel, Lyons (FR); Hans-Ludwig Elbe, Wuppertal (DE); Jörg Nico Greul, Leichlingen (DE); Herbert Gayer, Monheim (DE); Ulrike Wachendorff-Neumann, Neuwied (DE); Peter Dahmen, Neuss (DE); Arnd Voerste, Köln (DE)

(73) Assignee: Bayer CropScience AG, Monheim (DE)

( * ) Notice: Subject to any disclaimer, the term of this patent is extended or adjusted under 35 U.S.C. 154(b) by 203 days.

(21) Appl. No.: 12/097,511

(22) PCT Filed: Dec. 5, 2006

(86) PCT No.: PCT/EP2006/011649

§ 371 (c)(1),
(2), (4) Date: Dec. 1, 2008

(87) PCT Pub. No.: WO2007/068373

PCT Pub. Date: Jun. 21, 2007

(65) Prior Publication Data

US 2009/0176844 A1   Jul. 9, 2009

(30) Foreign Application Priority Data

Dec. 17, 2005   (DE) ................. 10 2005 060 467

(51) Int. Cl.
*A61K 31/4152* (2006.01)
*C07D 231/12* (2006.01)
(52) U.S. Cl. .................................. 514/406; 548/374.1
(58) Field of Classification Search .................. 514/406; 548/374.1
See application file for complete search history.

(56) References Cited

U.S. PATENT DOCUMENTS

| 4,382,954 | A | 5/1983 | Chan |
| 5,093,347 | A | 3/1992 | Graneto et al. |
| 5,330,995 | A | 7/1994 | Eicken et al. |
| 5,914,344 | A | 6/1999 | Yoshikawa et al. |
| 5,922,732 | A | 7/1999 | Urch et al. |
| 2002/0061913 | A1 | 5/2002 | Urch et al. |

FOREIGN PATENT DOCUMENTS

| EP | 0 434 357 A2 | 6/1991 |
| JP | 3152353 | 6/1991 |
| JP | 09-132567 | 5/1997 |
| WO | WO 96/37494 | 11/1996 |
| WO | WO 98/25923 | 6/1998 |
| WO | WO 03/070705 A1 | 8/2003 |

*Primary Examiner*—Kamal A Saeed
*Assistant Examiner*—Samantha L Shterengarts
(74) *Attorney, Agent, or Firm*—Baker Donelson Bearman, Caldwell & Berkowitz, PC

(57) ABSTRACT

Novel carboxamides of the formula (I)

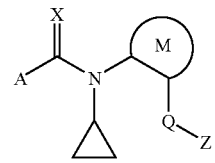

The present application also relates to a plurality of processes for preparing these compounds and their use for controlling unwanted microorganisms, and also novel intermediates and their preparation.

9 Claims, No Drawings

CARBOXAMIDES

CROSS REFERENCE TO RELATED APPLICATIONS

This application is a §371 National Stage Application of PCT/EP2006/011649 filed Dec. 5, 2006 which claims priority from German Application 10 2005 060 467.6 filed Dec. 13, 2005, the content of which is incorporated by reference.

BACKGROUND OF THE INVENTION

1. Field of the Invention

The present invention relates to novel carboxamides, to a plurality of processes for their preparation and to their use for controlling harmful microorganisms in crop protection and in the protection of materials.

2. Description of Related Art

It is already known that numerous carboxamides have fungicidal properties (cf., for example, WO 03/070705, EP-A 0 545 099 and JP-A 9-132567). The activity of the compounds described in these publications is good; however, it is sometimes unsatisfactory at low application rates.

SUMMARY OF THE INVENTION

This invention now provides novel carboxamides of the formula (I)

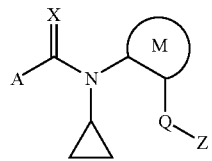

(I)

in which

X represents O (oxygen) or S (sulphur),

M represents a phenyl, thiophene, pyridine, pyrimidine, pyridazine or pyrazine ring, each of which is monosubstituted by $R^1$, or represents a thiazol ring which is substituted by $R^2$, $R^1$ represents hydrogen, fluorine, chlorine, methyl isopropyl, methylthio or trifluoromethyl, $R^2$ represents hydrogen, methyl, methylthio or trifluoromethyl, Q represents a direct bond, $C_1$-$C_4$-alkylene, $C_2$-$C_4$-alkenylene, O, S, SO, $SO_2$ or $NR^3$, $R^3$ represents hydrogen, $C_1$-$C_8$-alkyl, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-halogenalkyl, $C_2$-$C_6$-halogenalkenyl, $C_2$-$C_6$-halogenalkynyl or $C_3$-$C_6$-cycloalkyl, Z represents $Z^1$, $Z^2$, $Z^3$, $Z^4$, $Z^5$ or $Z^6$, $Z^1$ represents a phenyl which is optionally mono- to pentasubstituted by identical or different substituents, $Z^2$ represents pyridinyl which is optionally mono- to trisubstituted by identical or different substituents, $Z^3$ represents cycloalkyl or bicycloalkyl, each of which is optionally mono- or polysubstituted by identical or different substituents from the group consisting of halogen, alkyl and/or —$(CR^4R^5)_m SiR^6R^7R^8$, $Z^4$ represents unsubstituted $C_2$-$C_{20}$-alkyl or represents $C_1$-$C_{20}$-alkyl which is mono- or polysubstituted by identical or different substituents from the group consisting of halogen, alkylthio, alkylsulphinyl, alkylsulphonyl, alkoxy, alkylamino, dialkylamino, halogenalkylthio, halogenalkylsulphinyl, halogenalkylsulphonyl, halogenalkoxy, halogenalkylamino, halogen-dialkylamino, —$SiR^6R^7R^8$ and $C_3$-$C_6$-cycloalkyl, where the cycloalkyl moiety for its part may optionally be mono- or polysubstituted by identical or different substituents from the group consisting of halogen and $C_1$-$C_4$-alkyl, $Z^5$ represents $C_2$-$C_{20}$-alkenyl or $C_2$-$C_{20}$-alkynyl, each of which is optionally mono- or polysubstituted by identical or different substituents from the group consisting of halogen, alkylthio, alkylsulphinyl, alkylsulphonyl, alkoxy, alkylamino, dialkylamino, halogenalkylthio, halogenalkylsulphinyl, halogenalkylsulphonyl, halogenalkoxy, halogenalkylamino, halogen-dialkylamino, —$SiR^6R^7R^8$ and $C_3$-$C_6$-cycloalkyl, where the cycloalkyl moiety for its part may optionally be mono- or polysubstituted by identical or different substituents from the group consisting of halogen and $C_1$-$C_4$-alkyl, $Z^6$ represents a saturated or unsaturated 3- to 7-membered ring which is optionally mono- or polysubstituted and which contains a silicon atom as ring member, in which case Q represents a direct bond or $C_1$-$C_4$-alkylene, $R^4$ represents hydrogen or $C_1$-$C_4$-alkyl, $R^5$ represents hydrogen or $C_1$-$C_4$-alkyl, m represents 0, 1, 2 or 3, $R^6$ and $R^7$ independently of one another represent hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-halogenalkyl, $R^8$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-halogenalkyl, $C_2$-$C_6$-halogenalkenyl, $C_2$-$C_6$-halogen-alkynyl, $C_3$-$C_6$-cycloalkyl, or represents in each case optionally substituted phenyl or phenylalkyl, or M-Q-Z together represent 1H-2,3-dihydro-inden-4-yl, 1,3-dihydro-2-benzofuran-4-yl or 1,3-dihydro-2-benzothien-4-yl, each of which is optionally mono- to trisubstituted by methyl, A represents one of the radicals A1 to A19 below

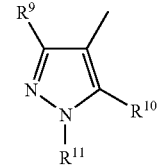

A1

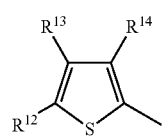

A2

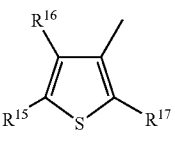

A3

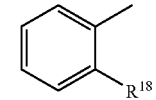

A4

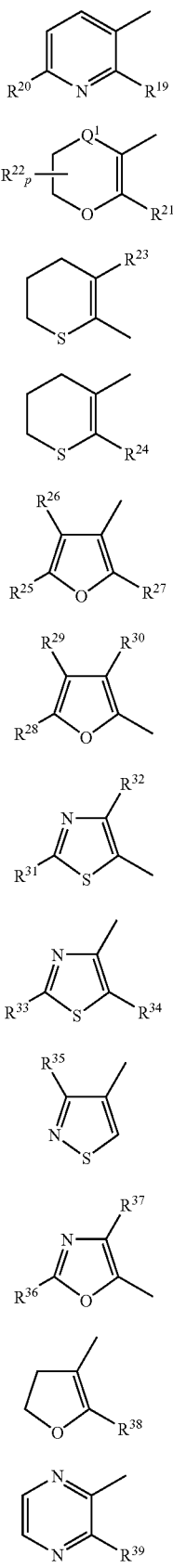

R⁹ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-halogenalkyl, $C_1$-$C_4$-halogenalkoxy or $C_1$-$C_4$-halogenalkylthio having in each case 1 to 5 halogen atoms, aminocarbonyl or aminocarbonyl-$C_1$-$C_4$-alkyl, R¹⁰ represents hydrogen, halogen, cyano, $C_1$-$C_4$-alkyl, $C_1$-$C_4$-alkoxy or $C_1$-$C_4$-alkylthio, R¹¹ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-halogenalkyl, $C_1$-$C_4$-halogenalkylthio-$C_1$-$C_4$-alkyl, $C_1$-$C_4$-halogenalkoxy-$C_1$-$C_4$-alkyl having in each case 1 to 5 halogen atoms, or phenyl, R¹² and R¹³ independently of one another represent hydrogen, halogen, $C_1$-$C_4$-alkyl or $C_1$-$C_4$-halogenalkyl having 1 to 5 halogen atoms, R¹⁴ represents halogen, cyano or $C_1$-$C_4$-alkyl, or $C_1$-$C_4$-halogenalkyl or $C_1$-$C_4$-halogenalkoxy having in each case 1 to 5 halogen atoms, R¹⁵ and R¹⁶ independently of one another represent hydrogen, halogen, $C_1$-$C_4$-alkyl or $C_1$-$C_4$-halogenalkyl having 1 to 5 halogen atoms, R¹⁷ represents hydrogen, halogen, $C_1$-$C_4$-alkyl or $C_1$-$C_4$-halogenalkyl having 1 to 5 halogen atoms, R¹⁸ represents hydrogen, halogen, hydroxy, cyano, $C_1$-$C_6$-alkyl, $C_1$-$C_4$-halogenalkyl, $C_1$-$C_4$-halogenalkoxy or $C_1$-$C_4$-halogenalkylthio having in each case 1 to 5 halogen atoms, R¹⁹ represents halogen, hydroxy, cyano, $C_1$-$C_4$-alkyl, $C_1$-$C_4$-alkoxy, $C_1$-$C_4$-alkylthio, $C_1$-$C_4$-halogenalkyl, $C_1$-$C_4$-halogenalkylthio or $C_1$-$C_4$-halogenalkoxy having in each case 1 to 5 halogen atoms, R²⁰ represents hydrogen, halogen, cyano, $C_1$-$C_4$-alkyl, $C_1$-$C_4$-alkoxy, $C_1$-$C_4$-alkylthio, $C_1$-$C_4$-halogenalkyl, $C_1$-$C_4$-halogenalkoxy having in each case 1 to 5 halogen atoms, $C_1$-$C_4$-alkylsulphinyl or $C_1$-$C_4$-alkylsulphonyl, R²¹ represents $C_1$-$C_4$-alkyl or $C_1$-$C_4$-halogenalkyl having 1 to 5 halogen atoms, R²² represents $C_1$-$C_4$-alkyl, Q¹ represents S (sulphur), SO, $SO_2$ or $CH_2$, p represents 0, 1 or 2, where R²² represents identical or different radicals if p represents 2, R²³ represents $C_1$-$C_4$-alkyl or $C_1$-$C_4$-halogenalkyl having 1 to 5 halogen atoms, R²⁴ represents $C_1$-$C_4$-alkyl or $C_1$-$C_4$-halogenalkyl having 1 to 5 halogen atoms, $R^{25}$ and $R^{26}$ independently of one another represent hydrogen, halogen, amino, $C_1$-$C_4$-alkyl or $C_1$-$C_4$-halogenalkyl having 1 to 5 halogen atoms, $R^{27}$ represents hydrogen, halogen, $C_1$-$C_4$-alkyl or $C_1$-$C_4$-halogenalkyl having 1 to 5 halogen atoms, $R^{28}$ and $R^{29}$ independently of one another represent hydrogen, halogen, amino, nitro, $C_1$-$C_4$-alkyl or $C_1$-$C_4$-halogenalkyl having 1 to 5 halogen atoms, $R^{30}$ represents hydrogen, halogen, $C_1$-$C_4$-alkyl or $C_1$-$C_4$-halogenalkyl having 1 to 5 halogen atoms, $R^{31}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-halogenalkyl having 1 to 5 halogen atoms, $R^{32}$ represents halogen, $C_1$-$C_4$-alkyl or $C_1$-$C_4$-halogenalkyl having 1 to 5 halogen atoms, $R^{33}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-halogenalkyl having 1 to 5 halogen atoms, $R^{34}$ represents halogen, $C_1$-$C_4$-alkyl or $C_1$-$C_4$-halogenalkyl having 1 to 5 halogen atoms, $R^{35}$ represents halogen, $C_1$-$C_4$-alkyl or $C_1$-$C_4$-halogenalkyl having 1 to 5 halogen atoms, $R^{36}$ represents hydrogen or $C_1$-$C_4$-alkyl, $R^{37}$ represents halogen or $C_1$-$C_4$-alkyl, $R^{38}$ represents $C_1$-$C_4$-alkyl or $C_1$-$C_4$-halogenalkyl having 1 to 5 halogen atoms, $R^{39}$ represents hydrogen, halogen, $C_1$-$C_4$-alkyl or $C_1$-$C_4$-halogenalkyl having 1 to 5 halogen atoms, $R^{40}$ represents halogen, hydroxy, $C_1$-$C_4$-alkyl, $C_1$-$C_4$-alkoxy, $C_1$-$C_4$-alkylthio, $C_1$-$C_4$-halogenalkyl, $C_1$-$C_4$-halogenalkylthio or $C_1$-$C_4$-halogenalkoxy having in each case 1 to 5 halogen atoms, $R^{41}$ represents hydrogen, cyano, $C_1$-$C_4$-alkyl, $C_1$-$C_4$-halogenalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkylsulphonyl, di($C_1$-$C_4$-alkyl)aminosulphonyl, $C_1$-$C_6$-alkylcarbonyl or in each case optionally substituted phenylsulphonyl or benzoyl, $R^{42}$ represents hydrogen, halogen, $C_1$-$C_4$-alkyl or $C_1$-$C_4$-halogenalkyl having 1 to 5 halogen atoms, $R^{43}$ represents hydrogen, halogen, cyano, $C_1$-$C_4$-alkyl or $C_1$-$C_4$-halogenalkyl having 1 to 5 halogen atoms, $R^{44}$ represents hydrogen, halogen, $C_1$-$C_4$-alkyl or $C_1$-$C_4$-halogenalkyl having 1 to 5 halogen atoms, $R^{45}$ represents $C_1$-$C_4$-alkyl.

DETAILED DESCRIPTION OF A PREFERRED EMBODIMENT

Furthermore, it has been found that carboxamides of the formula (I) are obtained when (a) carbonyl halides of the formula (II)

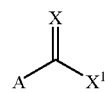
(II)

in which

A and X are as defined above, $X^1$ represents halogen or hydroxy, are reacted with cyclopropylamines of the formula (III)

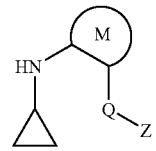
(III)

in which M, Q and Z are as defined above, if appropriate in the presence of a coupling agent, if appropriate in the presence of an acid binder and if appropriate in the presence of a diluent.

Finally, it has been found that the novel carboxamides of the formula (I) have very good microbicidal properties and can be used for controlling unwanted microorganisms both in crop protection and in the protection of materials.

If appropriate, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers, and also the threo and erythro, and the optical isomers, any mixtures of these isomers, and the possible tautomeric forms.

The formula (I) provides a general definition of the biphenylthiazolcarboxamides according to the invention. Preferred radical definitions of the formulae mentioned above and below are given below. These definitions apply to the end products of the formula (I) and likewise all intermediates.

X preferably represents O (oxygen).

X also preferably represents S (sulphur).

M preferably represents one of the cycles below

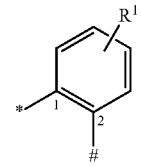
M-1

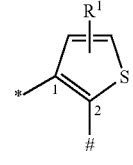
M-2

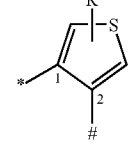
M-3

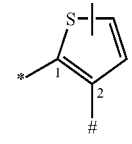
M-4

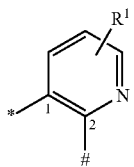
M-5

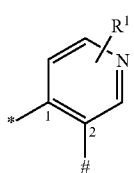
M-6

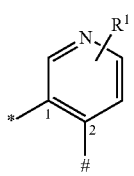
M-7

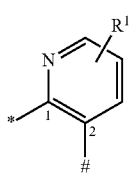
M-8

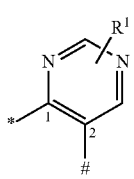
M-9

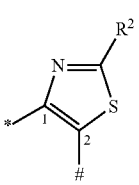
M-10

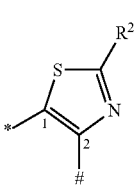
M-11

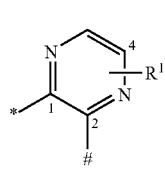
M-12

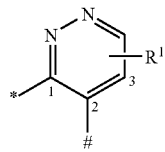
M-13

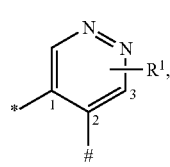
M-14 where the bond marked "*" is linked to the amide and the bond marked "#" is linked to the radical R.

M particularly preferably represents a cycle selected from the group consisting of M-1, M-2, M-3, M-4, M-5, M-6, M-9, M-10 and M-11.

M very particularly preferably represents a cycle selected from the group consisting of M-1, M-2, M-5, M-6, M-9, M-10 and M-11.

M especially preferably represents the cycle M-1.

M furthermore especially preferably represents the heterocycle M-2.

M furthermore especially preferably represents the heterocycle M-5.

M furthermore especially preferably represents the heterocycle M-6.

M furthermore especially preferably represents the heterocycle M-9.

M furthermore especially preferably represents the heterocycle M-10.

M furthermore especially preferably represents the heterocycle M-11.

$R^1$ preferably represents hydrogen.

$R^1$ furthermore, if M represents M-1, preferably represents fluorine, where fluorine is particularly preferably located in the 4-, 5- or 6-position, very particularly preferably in the 4- or 6-position, especially in the 4-position, of the anilide radical.

$R^1$ furthermore, if M represents M-1, preferably represents chlorine, where chlorine is particularly preferably located in the 5-position of the anilide radical.

$R^1$ furthermore, if M represents M-1, preferably represents methyl, where methyl is particularly preferably located in the 3-position of the anilide radical.

$R^1$ furthermore, if M represents M-1, preferably represents trifluoromethyl, where trifluoromethyl is particularly preferably located in the 4- or 5-position of the anilide radical.

$R^1$ furthermore, if M represents M-2, M-3 or M-4, preferably represents chlorine, where chlorine is particularly preferably located in the 5-position (M-2, M-3) or in the 3-position (M-4).

$R^1$ furthermore, if M represents M-2, M-3 or M-4, preferably represents methyl, where methyl is particularly preferably located in the 5-position (M-2, M-3) or in the 3-position (M-4).

$R^1$ furthermore, if M represents M-5, M-6, M-7 or M-8, preferably represents fluorine, where fluorine is particularly preferably located in the 6-position (M-5, M-6) or in the 3-position (M-7, M-8).

$R^1$ furthermore, if M represents M-5, M-6, M-7 or M-8, preferably represents chlorine, where chlorine is particularly preferably located in the 6-position (M-5, M-6) or in the 3-position (M-7, M-8).

$R^1$ furthermore, if M represents M-5, M-6, M-7 or M-8, preferably represents methyl, where methyl is particularly preferably located in the 4-position (M-5) or in the 3-position (M-6, M-7, M-8).

$R^1$ furthermore, if M represents M-9, preferably represents methyl, where methyl is particularly preferably located in the 3-position.

$R^1$ furthermore, if M represents M-9, preferably represents trifluoromethyl, where trifluoromethyl is particularly preferably located in the 3-position.

$R^1$ furthermore, if M represents M-12, preferably represents methyl, where methyl is particularly preferably located in the 4-position.

$R^1$ furthermore, if M represents M-12, preferably represents trifluoromethyl, where trifluoromethyl is particularly preferably located in the 4-position.

$R^1$ furthermore, if M represents M-13, preferably represents methyl, where methyl is particularly preferably located in the 3-position.

$R^1$ furthermore, if M represents M-13, preferably represents trifluoromethyl, where trifluoromethyl is particularly preferably located in the 3-position.

$R^1$ furthermore, if M represents M-14, preferably represents methyl, where methyl is particularly preferably located in the 3-position.

$R^1$ furthermore, if M represents M-14, preferably represents trifluoromethyl, where trifluoromethyl is particularly preferably located in the 3-position.

$R^2$ preferably represents hydrogen.

$R^2$ furthermore preferably represents methyl.

$R^2$ furthermore preferably represents trifluoromethyl.

Q preferably represents a direct bond.

Q furthermore preferably represents —$CH_2$—, —$(CH_2)_2$—, —$(CH_2)_3$—, —$CH(CH_3)$—, —$C(CH_3)_2$—, particularly preferably represents —$CH_2$—, —$(CH_2)_2$—, —$CH(CH_3)$—.

Q furthermore preferably represents —CH═CH—, —$CH_2$—CH═CH—, —$CH(CH_3)$—CH═CH—, particularly preferably represents —CH═CH—, —$CH_2$—CH═CH—.

Q furthermore preferably represents O.

Q furthermore preferably represents S.

Q furthermore preferably represents SO.

Q furthermore preferably represents $SO_2$.

Q furthermore preferably represents $NR^3$, particularly preferably NH.

$R^3$ preferably represents hydrogen, $C_1$-$C_6$-alkyl, $C_1$-$C_3$-alkoxy-$C_1$-$C_3$-alkyl, $C_1$-$C_3$-alkylthio-$C_1$-$C_3$-alkyl or $C_3$-$C_6$-cycloalkyl.

$R^3$ particularly preferably represents hydrogen, methyl, ethyl, n- or isopropyl, n-, sec-, iso- or tert-butyl, methoxymethyl, ethoxymethyl, methoxyethyl, ethoxyethyl, methylthiomethyl, ethylthiomethyl, methylthioethyl, ethylthioethyl or cyclopropyl.

$R^3$ very particularly preferably represents hydrogen, methyl, ethyl, n- or isopropyl, iso- or tert-butyl, methoxymethyl or methylthiomethyl.

Z preferably represents $Z^1$.

$Z^1$ preferably represents phenyl which is optionally mono- to pentasubstituted by identical or different substituents, where the substituents are in each case selected from the list $W^1$.

$Z^1$ particularly preferably represents monosubstituted phenyl, where the substituents are selected from the list $W^1$.

$Z^1$ also particularly preferably represents phenyl which is disubstituted by identical or different substituents, where the substituents are selected from the list $W^1$.

$Z^1$ also particularly preferably represents phenyl which is trisubstituted by identical or different substituents, where the substituents are selected from the list $W^1$.

$Z^1$ very particularly preferably represents phenyl which is monosubstituted in the 4-position, where the substituents are selected from the list $W^1$.

$Z^1$ very particularly preferably represents phenyl which is disubstituted by identical or different substituents in the 3,4-position, where the substituents are selected from the list $W^1$.

$Z^1$ very particularly preferably represents phenyl which is disubstituted by identical or different substituents in the 2,3-position, where the substituents are selected from the list $W^1$.

$Z^1$ very particularly preferably represents phenyl which is disubstituted by identical or different substituents in the 2,4-position, where the substituents are selected from the list $W^1$.

$Z^1$ very particularly preferably represents phenyl which is disubstituted by identical or different substituents in the 3,5-position, where the substituents are selected from the list $W^1$.

$Z^1$ very particularly preferably represents phenyl which is trisubstituted by identical or different substituents in the 2,4,6-position, where the substituents are selected from the list $W^1$.

$W^1$ represents halogen, cyano, nitro, amino, hydroxyl, formyl, carboxy, carbamoyl, thiocarbamoyl;

in each case straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;

in each case straight-chain or branched alkenyl or alkenyloxy having in each case 2 to 6 carbon atoms;

in each case straight-chain or branched haloalkyl, haloalkoxy, haloalkylthio, haloalkylsulphinyl or haloalkylsulphonyl having in each case 1 to 6 carbon atoms and 1 to 13 identical or different halogen atoms;

in each case straight-chain or branched haloalkenyl or haloalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylaminocarbonyl, dialkylaminocarbonyl, aiylalkylaminocarbonyl, dialkylaminocarbonyloxy having 1 to 6 carbon atoms in the respective hydrocarbon chains, alkenylcarbonyl or alkynylcarbonyl, having 2 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which radicals is optionally mono- to tetrasubstituted by identical or different substituents from the group consisting of fluorine, chlorine, oxo, methyl, trifluoromethyl and ethyl;

or the groupings —$(CR^4R^5)_m SiR^6R^7R^8$ or —$C(Q^2)$═N-$Q^3$, in which $Q^2$ represents hydrogen, hydroxyl or alkyl having 1 to 4 carbon atoms, haloalkyl having 1 to 4 carbon atoms and 1 to 9 fluorine, chlorine and/or bromine atoms or cycloalkyl having 1 to 6 carbon atoms and $Q^3$ represents hydroxyl, amino, methylamino, phenyl, benzyl or represents in each case optionally cyano-, hydroxyl-, alkoxy-, alkylthio-, alkylamino-, dialkylamino- or phenyl-substituted alkyl or alkoxy having 1 to 4 carbon atoms, or represents alkenyloxy or alkynyloxy having in each case 2 to 4 carbon atoms, and also phenyl, phenoxy, phenylthio, benzoyl, benzoylethenyl, cinnamoyl, heterocyclyl or phenylalkyl, phenylalkyloxy, phenylalkylthio or heterocyclylalkyl having in each case 1 to 3 carbon atoms in the respective alkyl moieties, each of which radicals is optionally mono- to trisubstituted in the ring moiety by halogen and/or straight-chain or branched alkyl or alkoxy having 1 to 4 carbon atoms.

$W^1$ preferably represents fluorine, chlorine, bromine, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, in each case doubly attached difluoromethylenedioxy or tetrafluoroethylenedioxy, or the groupings —$CH_2Si(CH_3)_3$, —$Si(CH_3)_3$ or —$C(Q^2)$=N-$Q^3$, in which $Q^2$ represents hydrogen, methyl, ethyl or trifluoromethyl and $Q^3$ represents hydroxyl, methoxy, ethoxy, propoxy or isopropoxy.

Z preferably represents $Z^2$ $Z^2$ preferably represents 2-pyridinyl, 3-pyridinyl or 4-pyridinyl, each of which is optionally mono- to trisubstituted by identical or different substituents, where the substituents are in each case selected from the list $W^2$.

$Z^2$ particularly preferably represents in each case monosubstituted 2-pyridinyl, 3-pyridinyl or 4-pyridinyl, where the substituents are in each case selected from the list $W^2$.

$Z^2$ also particularly preferably represents 2-pyridinyl, 3-pyridinyl or 4-pyridinyl, each of which is disubstituted by identical or different substituents, where the substituents are in each case selected from the list $W^2$.

$Z^2$ also particularly preferably represents 2-pyridinyl, 3-pyridinyl or 4-pyridinyl, each of which is trisubstituted by identical or different substituents, where the substituents are in each case selected from the list $W^2$.

$Z^2$ very particularly preferably represents 2-pyridinyl which is monosubstituted in the 5-position or 3-pyridinyl which is monosubstituted in the 6-position, where the substituents are in each case selected from the list $W^2$.

$Z^2$ very particularly preferably represents 2-pyridinyl which is disubstituted by identical or different substituents in the 3,5-position, where the substituents are selected from the list $W^2$.

$Z^2$ very particularly preferably represents 3-pyridinyl which is disubstituted by identical or different substituents in the 4,6-position, where the substituents are selected from the list $W^2$.

$Z^2$ very particularly preferably represents 4-pyridinyl which is disubstituted by identical or different substituents in the 3,5-position, where the substituents are selected from the list $W^2$.

$W^2$ represents hydrogen, halogen, cyano, nitro, $C_1$-$C_6$-alkyl, $C_2$-$C_4$-alkenyl, $C_2$-$C_4$-alkynyl, $C_1$-$C_4$-alkoxy, $C_1$-$C_4$-alkylthio, $C_1$-$C_4$-alkylsulphinyl, $C_1$-$C_4$-alkylsulphonyl, $C_3$-$C_6$-cycloalkyl; represents $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 5 halogen atoms; represents —$SO_2NR^{46}R^{47}$, —$C(=X)R^{48}$, —$Si(R^{49})_3$, $C_2$-$C_4$-alkenylene-$Si(R^{49})_3$, $C_2$-$C_4$-alkynylene-$Si(R^{49})_3$, —$NR^{46}R^{47}$, —$CH_2$—$NR^{46}R^{47}$, in which
$R^{46}$ represents hydrogen, $C_1$-$C_4$-alkyl or —$C(=X)R^{48}$,
$R^{47}$ represents hydrogen, $C_1$-$C_4$-alkyl or —$C(=X)R^{48}$,
$R^{46}$ and $R^{47}$ furthermore together with the nitrogen atom to which they are attached form a saturated heterocycle which has 5 to 8 ring atoms and is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and $NR^{50}$, $R^{48}$ represents hydrogen, $C_1$-$C_4$-alkyl, $C_1$-$C_4$-alkoxy or —$NR^{51}R^{52}$, $R^{49}$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl, where the three radicals $R^{49}$ may in each case be identical or different, $R^{50}$ represents hydrogen or $C_1$-$C_6$-alkyl,
$R^{51}$ represents hydrogen or $C_1$-$C_4$-alkyl,
$R^{52}$ represents hydrogen or $C_1$-$C_4$-alkyl,
$R^{51}$ and $R^{52}$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and $NR^{50}$, $W^2$ preferably represents hydrogen, fluorine, chlorine, bromine, cyano, nitro, methyl, ethyl, n- or isopropyl, n-, iso-, sec- or tert-butyl, allyl, propargyl, methoxy, ethoxy, n- or isopropoxy, n-, iso-, sec- or tert-butoxy, methylthio, ethylthio, n- or isopropylthio, n-, iso-, sec- or tert-butylthio, methylsulphinyl, ethylsulphinyl, n- or isopropylsulphinyl, n-, iso-, sec- or tert-butylsulphinyl, methylsulphonyl, ethylsulphonyl, n- or iso-propylsulphonyl, n-, iso-, sec- or tert-butylsulphonyl, cyclopropyl, cyclopentyl, cyclohexyl, trifluoromethyl, difluoromethyl, trichloromethyl, trifluoroethyl, trifluoromethoxy, difluoromethoxy, trichloromethoxy, difluoromethylthio, difluorochloromethylthio, trifluoromethylthio, trifluoromethylsulphinyl, trifluoromethylsulphonyl, —$SO_2NMe_2$, —$C(=X)R^{48}$, —$Si(R^{49})_3$, —CH=CH—$Si(R^{49})_3$, —$CH_2$—CH=CH—$Si(R^{49})_3$, —CH=CH—$CH_2$—$Si(R^{49})_3$, —C≡C—$Si(R^{49})_3$, —$CH_2$—C≡C—$Si(R^{49})_3$, —C≡C—$CH_2$—$Si(R^{49})_3$, —$CH_2$—C≡C—$CH_2$—$Si(R^{49})_3$, —$NR^{46}R^{47}$, —$CH_2$—$NR^{46}R^{47}$.

$R^{46}$ preferably represents hydrogen, methyl, ethyl, n- or isopropyl or —$C(=X)R^{48}$.

$R^{46}$ particularly preferably represents hydrogen or methyl.

$R^{47}$ preferably represents hydrogen, methyl, ethyl, n- or isopropyl or —$C(=X)R^{48}$.

$R^{47}$ particularly preferably represents hydrogen or methyl.

$R^{46}$ and $R^{47}$ furthermore together with the nitrogen atom to which they are attached preferably form a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by $R^{50}$ $R^{48}$ preferably represents hydrogen, methyl, ethyl, n- or isopropyl, methoxy, ethoxy, n- or isopropoxy or —$NR^{51}R^{52}$.

$R^{48}$ particularly preferably represents hydrogen, methyl, ethyl, methoxy, ethoxy or —$NR^{51}R^{52}$.

$R^{49}$ preferably represents methyl, ethyl, methoxy, ethoxy, methoxymethyl, ethoxymethyl, methoxyethyl, ethoxyethyl, methylthiomethyl, ethylthiomethyl, methylthioethyl or ethylthioethyl, where the three radicals $R^{49}$ may in each case be identical or different.

$R^{49}$ particularly preferably represents methyl, methoxy, methoxymethyl or methylthiomethyl, where the three radicals $R^{49}$ may in each case be identical or different.

$R^{49}$ very particularly preferably represents methyl.

$R^{50}$ preferably represents hydrogen or $C_1$-$C_4$-alkyl.

$R^{50}$ particularly preferably represents hydrogen, methyl, ethyl, n- or isopropyl, n-, iso-, sec- or tert-butyl.

$R^{51}$ preferably represents hydrogen, methyl, ethyl, n- or isopropyl.

$R^{51}$ particularly preferably represents hydrogen or methyl.

$R^{52}$ preferably represents hydrogen, methyl, ethyl, n- or isopropyl.

$R^{52}$ particularly preferably represents hydrogen or methyl.

$R^{51}$ and $R^{52}$ furthermore together with the nitrogen atom to which they are attached preferably form a heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by $R^{50}$.

Z also preferably represents $Z^3$.

$Z^3$ preferably represents cycloalkyl or bicycloalkyl having in each case 3 to 10 carbon atoms, each of which radicals is optionally mono- to tetrasubstituted by identical or different substituents from the group consisting of halogen, $C_1$-$C_4$-alkyl, —$CH_2Si(CH_3)_3$ and —$Si(CH_3)_3$.

$Z^3$ particularly preferably represents cyclopropyl, cyclopentyl, cyclohexyl, cycloheptyl, cyclooctyl, cyclononyl, bicyclo[2.2.1]heptyl or bicyclo[2.2.2]octyl, each of which is optionally mono- to tetrasubstituted by identical or different substituents from the group consisting of chlorine, methyl, —$CH_2Si(CH_3)_3$ and —$Si(CH_3)_3$.

$Z^3$ very particularly preferably represents chlorine- and methyl-substituted cyclopropyl.

Z also preferably represents $Z^4$.

$Z^4$ preferably represents unsubstituted $C_2$-$C_{20}$-alkyl or represents $C_1$-$C_{20}$-alkyl which is mono- or polysubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^6R^7R^8$ and $C_3$-$C_6$-cycloalkyl, where the cycloalkyl moiety for its part may optionally be mono- or polysubstituted by identical or different substituents from the group consisting of fluorine, chlorine, bromine, iodine, $C_1$-$C_4$-alkyl and $C_1$-$C_4$-haloalkyl.

$Z^4$ particularly preferably represents unsubstituted $C_2$-$C_{20}$-alkyl.

$Z^4$ also particularly preferably represents $C_1$-$C_{20}$-alkyl which is substituted by fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^6R^7R^8$, cyclopropyl, dichlorocyclopropyl, cyclobutyl, cyclopentyl or cyclohexyl; very particularly preferably $C_1$-$C_{20}$-alkyl which is substituted by fluorine, chlorine, methylthio, ethylthio, n- or isopropylthio, n-, iso-, sec-, tert-butylthio, pentylthio, hexylthio, methylsulphonyl, ethylsulphonyl, n- or isopropylsulphonyl, n-, iso-, sec-, tert-butylsulphonyl, methoxy, ethoxy, n- or isopropoxy, n-, iso-, sec-, tert-butoxy, methylamino, ethylamino, n- or isopropylamino, n-, iso-, sec-, tert-butylamino, dimethylamino, diisopropylamino, trifluoromethylthio, trifluoromethoxy, —$SiR^6R^7R^8$, cyclopropyl, dichlorocyclopropyl, cyclobutyl, cyclopentyl or cyclohexyl.

Z also preferably represents $Z^5$.

$Z^5$ preferably represents $C_2$-$C_{20}$-alkenyl or $C_2$-$C_{20}$-alkynyl, each of which is optionally mono- or polysubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^6R^7R^8$ and $C_3$-$C_6$-cycloalkyl, where the cycloalkyl moiety for its part may optionally be mono- to tetrasubstituted by identical or different substituents from the group consisting of fluorine, chlorine, bromine, iodine, $C_1$-$C_4$-alkyl and $C_1$-$C_4$-haloalkyl.

$Z^5$ particularly preferably represents $C_2$-$C_{20}$-alkenyl or $C_2$-$C_{20}$-alkynyl, each of which is optionally substituted by fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^6R^7R^8$, cyclopropyl, dichlorocyclopropyl, cyclobutyl, cyclopentyl or cyclohexyl.

$Z^5$ very particularly preferably represents $C_2$-$C_{20}$-alkenyl or $C_2$-$C_{20}$-alkynyl.

Z also preferably represents $Z^6$.

$Z^6$ preferably represents one of the rings below

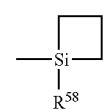
Si-1

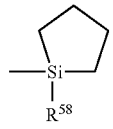
Si-2

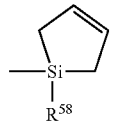
Si-3

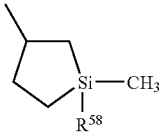
Si-4

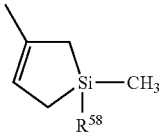
Si-5

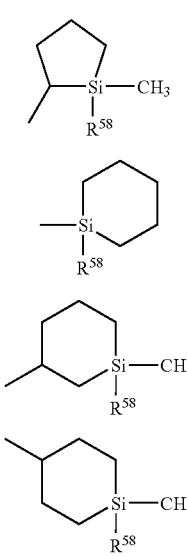

Si-6

Si-7

Si-8

Si-9 in which $R^{58}$ represents hydrogen or methyl.

$R^4$ preferably represents hydrogen or methyl.

$R^4$ particularly preferably represents hydrogen.

$R^5$ preferably represents hydrogen or methyl.

$R^5$ particularly preferably represents hydrogen.

m preferably represents 0, 1 or 2.

$R^6$ and $R^7$ independently of one another preferably represent $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl.

$R^6$ and $R^7$ independently of one another particularly preferably represent methyl, ethyl, methoxy, ethoxy, methoxymethyl, ethoxymethyl, methoxyethyl, ethoxyethyl, methylthiomethyl, ethylthiomethyl, methylthioethyl or ethylthioethyl.

$R^6$ and $R^7$ independently of one another very particularly preferably represent methyl, methoxy, methoxymethyl or methylthiomethyl.

$R^6$ and $R^7$ especially preferably each represent methyl.

$R^8$ preferably represents $C_1$-$C_6$-alkyl, $C_1$-$C_6$-alkoxy, $C_1$-$C_3$-alkoxy-$C_1$-$C_3$-alkyl, $C_1$-$C_3$-alkylthio-$C_1$-$C_3$-alkyl, $C_3$-$C_6$-cycloalkyl, phenyl or benzyl.

$R^8$ particularly preferably represents methyl, ethyl, n- or isopropyl, n-, sec-, iso- or tert-butyl, methoxy, ethoxy, n- or isopropoxy, n-, sec-, iso- or tert-butoxy, methoxymethyl, ethoxymethyl, methoxyethyl, ethoxyethyl, methylthiomethyl, ethylthiomethyl, methylthioethyl, ethylthioethyl, cyclopropyl, phenyl or benzyl.

$R^8$ very particularly preferably represents methyl, ethyl, n- or isopropyl, iso- or tert-butyl, methoxy, isopropoxy, iso- or tert-butoxy, methoxymethyl, methylthiomethyl or phenyl.

$R^8$ especially preferably represents methyl, ethyl, n- or isopropyl, iso- or tert-butyl, methoxy, isopropoxy, iso- or tert-butoxy.

$R^8$ most preferably represents methyl.

M-Q-Z also preferably together represent 1,1,3-trimethyl-1H-2,3-dihydroinden-4-yl, 1,3-dimethyl-1H-2,3-dihydroinden-4-yl, 1,1,3-trimethyl-1,3-dihydro-2-benzofuran-4-yl, 1,3-dimethyl-1,3-dihydro-2-benzofuran-4-yl, 1,1,3-trimethyl-1,3-dihydro-2-benzothien-4-yl or 1,3-dimethyl-1,3-dihydro-2-benzothien-4-yl.

M-Q-Z also particularly preferably together represent 1,1,3-trimethyl-1H-2,3-dihydroinden-4-yl.

A preferably represents one of the radicals A1, A2, A3, A4, A5, A6, A9, A10, A1, A12 or A 17.

A particularly preferably represents one of the radicals A1, A2, A4, A5, A6, A9, A11, A16, A17.

A very particularly preferably represents the radical A1.

A furthermore very particularly preferably represents the radical A2.

A furthermore very particularly preferably represents the radical A4.

A furthermore very particularly preferably represents the radical A5.

A furthermore very particularly preferably represents the radical A6.

A furthermore very particularly preferably represents the radical A9.

A furthermore very particularly preferably represents the radical A11.

A furthermore very particularly preferably represents the radical A16.

A furthermore very particularly preferably represents the radical A17.

$R^9$ preferably represents hydrogen, cyano, fluorine, chlorine, bromine, iodine, methyl, ethyl, isopropyl, methoxy, ethoxy, methylthio, ethylthio, cyclopropyl, $C_1$-$C_2$-haloalkyl, $C_1$-$C_2$-haloalkoxy having in each case 1 to 5 fluorine, chlorine and/or bromine atoms, trifluoromethylthio, difluoromethylthio, aminocarbonyl, aminocarbonylmethyl or aminocarbonylethyl.

$R^9$ particularly preferably represents hydrogen, fluorine, chlorine, bromine, iodine, methyl, ethyl, isopropyl, monofluoromethyl, monofluoroethyl, difluoromethyl, trifluoromethyl, difluorochloromethyl, trichloromethyl, dichloromethyl, cyclopropyl, methoxy, ethoxy, trifluoromethoxy, trichloromethoxy, methylthio, ethylthio, trifluoromethylthio or difluoromethylthio.

$R^9$ very particularly preferably represents hydrogen, fluorine, chlorine, bromine, iodine, methyl, isopropyl, monofluoromethyl, monofluoroethyl, difluoromethyl, Trifluoromethyl, difluorochloromethyl or trichloromethyl.

$R^9$ especially preferably represents methyl, difluoromethyl, trifluoromethyl or 1-fluoroethyl.

$R^{10}$ preferably represents hydrogen, fluorine, chlorine, bromine, iodine, methyl, ethyl, methoxy, ethoxy, methylthio or ethylthio.

$R^{10}$ particularly preferably represents hydrogen, fluorine, chlorine, bromine, iodine or methyl.

$R^{10}$ very particularly preferably represents hydrogen, fluorine, chlorine or methyl.

$R^{11}$ preferably represents hydrogen, methyl, ethyl, n-propyl, isopropyl, $C_1$-$C_2$-haloalkyl having 1 to 5 fluorine, chlorine and/or bromine atoms, hydroxymethyl, hydroxyethyl, cyclopropyl, cyclopentyl, cyclohexyl or phenyl.

$R^{11}$ particularly preferably represents hydrogen, methyl, ethyl, isopropyl, trifluoromethyl, difluoromethyl, hydroxymethyl, hydroxyethyl or phenyl.

$R^{11}$ very particularly preferably represents hydrogen, methyl, trifluoromethyl or phenyl.

$R^{11}$ especially preferably represents methyl.

$R^{12}$ and $R^{13}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{12}$ and $R^{13}$ independently of one another particularly preferably represent hydrogen, fluorine, chlorine, bromine, methyl, ethyl, difluoromethyl, trifluoromethyl, difluorochloromethyl or trichloromethyl.

$R^{12}$ and $R^{13}$ independently of one another very particularly preferably represent hydrogen, fluorine, chlorine, bromine, methyl, ethyl, difluoromethyl, trifluoromethyl or trichloromethyl.

$R^{12}$ and $R^{13p}$ p each represent hydrogen.

$R^{14}$ preferably represents fluorine, chlorine, bromine, cyano, methyl, ethyl, $C_1$-$C_2$-haloalkyl or $C_1$-$C_2$-haloalkoxy having in each case 1 to 5 fluorine, chlorine and/or bromine atoms.

$R^{14}$ particularly preferably represents fluorine, chlorine, bromine, cyano, methyl, trifluoromethyl, trifluoromethoxy, difluoromethoxy, difluorochloromethoxy or trichloromethoxy.

$R^{14}$ very particularly preferably represents fluorine, chlorine, bromine, iodine, methyl, trifluoromethyl or trifluoromethoxy.

$R^{14}$ especially preferably represents methyl or trifluoromethyl.

$R^{15}$ and $R^{16}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{15}$ and $R^{16}$ independently of one another particularly preferably represent hydrogen, fluorine, chlorine, bromine, methyl, ethyl, difluoromethyl, trifluoromethyl, difluorochloromethyl or trichloromethyl.

$R^{15}$ and $R^{16}$ independently of one another very particularly preferably represent hydrogen, fluorine, chlorine, bromine, methyl, ethyl, difluoromethyl, trifluoromethyl or trichloromethyl.

$R^{15}$ and $R^{16}$ especially preferably each represent hydrogen.

$R^{17}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{17}$ particularly preferably represents hydrogen, fluorine, chlorine, bromine, iodine, methyl or trifluoromethyl.

$R^{17}$ very particularly preferably represents fluorine, chlorine, bromine, iodine, methyl or trifluoromethyl.

$R^{18}$ preferably represents hydrogen, fluorine, chlorine, bromine, iodine, hydroxyl, cyano, $C_1$-$C_4$-alkyl, $C_1$-$C_2$-haloalkyl, $C_1$-$C_2$-haloalkoxy or $C_1$-$C_2$-haloalkylthio having in each case 1 to 5 fluorine, chlorine and/or bromine atoms.

$R^{18}$ particularly preferably represents hydrogen, fluorine, chlorine, bromine, iodine, hydroxyl, cyano, methyl, ethyl, n-propyl, isopropyl, n-butyl, isobutyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

$R^{18}$ very particularly preferably represents hydrogen, fluorine, chlorine, bromine, iodine, methyl, difluoromethyl, trifluoromethyl or trichloromethyl.

$R^{18}$ especially preferable represents iodine, methyl, difluoromethyl or trifluoromethyl.

$R^{19}$ preferably represents fluorine, chlorine, bromine, iodine, hydroxyl, cyano, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{19}$ particularly preferably represents fluorine, chlorine, bromine, iodine, hydroxyl, cyano, methyl, ethyl, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{19}$ very particularly preferably represents fluorine, chlorine, bromine, iodine, methyl, trifluoromethyl, difluoromethyl or trichloromethyl.

$R^{20}$ preferably represents hydrogen, fluorine, chlorine, bromine, iodine, cyano, $C_1$-$C_4$-alkyl, methoxy, ethoxy, methylthio, ethylthio, $C_1$-$C_2$-haloalkyl or $C_1$-$C_2$-haloalkoxy having in each case 1 to 5 fluorine, chlorine and/or bromine atoms, $C_1$-$C_2$-alkylsulphinyl or $C_1$-$C_2$-alkylsulphonyl.

$R^{20}$ particularly preferably represents hydrogen, fluorine, chlorine, bromine, iodine, cyano, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methylsulphinyl or methylsulphonyl.

$R^{20}$ very particularly preferably represents hydrogen, fluorine, chlorine, bromine, iodine, n-propyl, isopropyl, n-butyl, isobutyl, sec-butyl, tert-butyl, trifluoromethyl, difluoromethyl, trichloromethyl, methylsulphinyl or methylsulphonyl.

$R^{20}$ represents hydrogen.

$R^{21}$ preferably represents methyl, ethyl or $C_1$-$C_2$-haloalkyl having 1 to 5 fluorine, chlorine and/or bromine atoms.

$R^{21}$ particularly preferably represents methyl, ethyl, trifluoromethyl, difluoromethyl, difluorochloromethyl or trichloromethyl.

$R^{22}$ preferably represents methyl or ethyl.

$R^{22}$ particularly preferably represents methyl.

$Q^1$ preferably represents S (sulphur), $SO_2$ or $CH_2$.

$Q^1$ particularly preferably represents S (sulphur) or $CH_2$.

$Q^1$ very particularly preferably represents S (sulphur).

p preferably represents 0 or 1.

p particularly preferably represents 0.

$R^{23}$ preferably represents methyl, ethyl or $C_1$-$C_2$-haloalkyl having 1 to 5 fluorine, chlorine and/or bromine atoms.

$R^{23}$ particularly preferably represents methyl, ethyl, trifluoromethyl, difluoromethyl, difluorochloromethyl or trichloromethyl.

$R^{23}$ very particularly preferably represents methyl, trifluoromethyl, difluoromethyl or trichloromethyl.

$R^{24}$ preferably represents methyl, ethyl or $C_1$-$C_2$-haloalkyl having 1 to 5 fluorine, chlorine and/or bromine atoms.

$R^{24}$ particularly preferably represents methyl, ethyl, trifluoromethyl, difluoromethyl, difluorochloromethyl or trichloromethyl.

$R^{24}$ very particularly preferably represents methyl, trifluoromethyl, difluoromethyl or trichloromethyl.

$R^{25}$ and $R^{26}$ independently of one another preferably represent hydrogen, fluorine, chlorine, bromine, amino, methyl, ethyl or $C_1$-$C_2$-haloalkyl having 1 to 5 fluorine, chlorine and/or bromine atoms.

$R^{25}$ and $R^{26}$ independently of one another particularly preferably represent hydrogen, fluorine, chlorine, bromine, methyl, ethyl, trifluoromethyl, difluoromethyl, difluorochloromethyl or trichloromethyl.

$R^{25}$ and $R^{26}$ independently of one another very particularly preferably represent hydrogen, fluorine, chlorine, bromine, methyl, trifluoromethyl, difluoromethyl or trichloromethyl.

$R^{25}$ and $R^{26}$ especially preferably each represent hydrogen.

$R^{27}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{27}$ particularly preferably represents hydrogen, fluorine, chlorine, bromine, iodine, methyl, ethyl, trifluoromethyl, difluoromethyl, difluorochloromethyl or trichloromethyl.

$R^{27}$ very particularly preferably represents hydrogen, fluorine, chlorine, bromine, iodine, methyl, trifluoromethyl, difluoromethyl or trichloromethyl.

$R^{27}$ especially preferably represents methyl.

$R^{28}$ and $R^{29}$ independently of one another preferably represent hydrogen, fluorine, chlorine, bromine, amino, nitro, methyl, ethyl or $C_1$-$C_2$-haloalkyl having 1 to 5 fluorine, chlorine and/or bromine atoms.

$R^{28}$ and $R^{29}$ independently of one another particularly preferably represent hydrogen, fluorine, chlorine, bromine, nitro, methyl, ethyl, trifluoromethyl, difluoromethyl, difluorochloromethyl or trichloromethyl.

$R^{28}$ and $R^{29}$ independently of one another very particularly preferably represent hydrogen, fluorine, chlorine, bromine, methyl, trifluoromethyl, difluoromethyl or trichloromethyl.

$R^{28}$ and $R^{29}$ each represent hydrogen.

$R^{30}$ preferably represents hydrogen, fluorine, chlorine, bromine, methyl, ethyl or $C_1$-$C_2$-haloalkyl having 1 to 5 fluorine, chlorine and/or bromine atoms.

$R^{30}$ particularly preferably represents hydrogen, fluorine, chlorine, bromine, methyl, ethyl, trifluoromethyl, difluoromethyl, difluorochloromethyl or trichloromethyl.

$R^{30}$ very particularly preferably represents hydrogen, fluorine, chlorine, bromine, methyl, trifluoromethyl, difluoromethyl or trichloromethyl.

$R^{30}$ especially preferably represents methyl.

$R^{31}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{31}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{31}$ very particularly preferably represents hydrogen, fluorine, chlorine, bromine, amino, methylamino, dimethylamino, methyl, trifluoromethyl, difluoromethyl or trichloromethyl.

$R^{31}$ especially preferably represents amino, methylamino, dimethylamino, methyl or trifluoromethyl.

$R^{32}$ preferably represents fluorine, chlorine, bromine, methyl, ethyl or $C_1$-$C_2$-haloalkyl having 1 to 5 fluorine, chlorine and/or bromine atoms.

$R^{32}$ particularly preferably represents fluorine, chlorine, bromine, methyl, ethyl, trifluoromethyl, difluoromethyl, difluorochloromethyl or trichloromethyl.

$R^{32}$ very particularly preferably represents fluorine, chlorine, bromine, methyl, trifluoromethyl, difluoromethyl or trichloromethyl.

$R^{32}$ especially preferably represents methyl, trifluoromethyl or difluoromethyl.

$R^{33}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{33}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{33}$ very particularly preferably represents hydrogen, fluorine, chlorine, bromine, amino, methylamino, dimethylamino, methyl, trifluoromethyl, difluoromethyl or trichloromethyl.

$R^{33}$ especially preferably represents amino, methylamino, dimethylamino, methyl or trifluoromethyl.

$R^{34}$ preferably represents fluorine, chlorine, bromine, methyl, ethyl or $C_1$-$C_2$-haloalkyl having 1 to 5 fluorine, chlorine and/or bromine atoms.

$R^{34}$ particularly preferably represents fluorine, chlorine, bromine, methyl, ethyl, trifluoromethyl, difluoromethyl, difluorochloromethyl or trichloromethyl.

$R^{34}$ very particularly preferably represents fluorine, chlorine, bromine, methyl, trifluoromethyl, difluoromethyl or trichloromethyl.

$R^{34}$ especially preferably represents methyl, trifluoromethyl or difluoromethyl.

$R^{35}$ preferably represents fluorine, chlorine, bromine, methyl, ethyl or $C_1$-$C_2$-haloalkyl having 1 to 5 fluorine, chlorine and/or bromine atoms.

$R^{35}$ particularly preferably represents fluorine, chlorine, bromine, methyl, ethyl, trifluoromethyl, difluoromethyl, difluorochloromethyl or trichloromethyl.

$R^{35}$ very particularly preferably represents fluorine, chlorine, bromine, methyl, trifluoromethyl, difluoromethyl or trichloromethyl.

$R^{36}$ preferably represents hydrogen, methyl or ethyl.

$R^{36}$ particularly preferably represents methyl.

$R^{37}$ preferably represents fluorine, chlorine, bromine, methyl or ethyl.

$R^{37}$ particularly preferably represents fluorine, chlorine or methyl.

$R^{38}$ preferably represents methyl, ethyl or $C_1$-$C_2$-haloalkyl having 1 to 5 fluorine, chlorine and/or bromine atoms.

$R^{38}$ particularly preferably represents methyl, ethyl, trifluoromethyl, difluoromethyl, difluoro-chloromethyl or trichloromethyl.

$R^{38}$ very particularly preferably represents methyl, trifluoromethyl, difluoromethyl or trichloromethyl.

$R^{38}$ especially preferably represents methyl or trifluoromethyl.

$R^{39}$ preferably represents hydrogen, fluorine, chlorine, bromine, methyl, ethyl or $C_1$-$C_2$-haloalkyl having 1 to 5 fluorine, chlorine and/or bromine atoms.

$R^{39}$ particularly preferably represents hydrogen, fluorine, chlorine, bromine, methyl or trifluoromethyl.

$R^{40}$ preferably represents fluorine, chlorine, bromine, iodine, hydroxyl, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{40}$ particularly preferably represents fluorine, chlorine, bromine, iodine, methyl, ethyl, n-propyl, isopropyl, n-butyl, isobutyl, sec-butyl, tert-butyl, trifluoromethyl, difluoromethyl, difluorochloromethyl or trichloromethyl.

$R^{40}$ very particularly preferably represents fluorine, chlorine, bromine, iodine, methyl, trifluoromethyl, difluoromethyl or trichloromethyl.

$R^{41}$ preferably represents hydrogen, methyl, ethyl, $C_1$-$C_2$-haloalkyl having 1 to 5 fluorine, chlorine and/or bromine atoms, $C_1$-$C_2$-alkoxy-$C_1$-$C_2$-alkyl, hydroxymethyl, hydroxyethyl, methylsulphonyl or dimethylaminosulphonyl.

$R^{41}$ particularly preferably represents hydrogen, methyl, ethyl, trifluoromethyl, methoxymethyl, ethoxymethyl, hydroxymethyl or hydroxyethyl.

$R^{41}$ very particularly preferably represents methyl or methoxymethyl.

$R^{42}$ preferably represents hydrogen, fluorine, chlorine, bromine, methyl, ethyl or $C_1$-$C_2$-haloalkyl having 1 to 5 fluorine, chlorine and/or bromine atoms.

$R^{42}$ particularly preferably represents hydrogen, fluorine, chlorine, bromine, methyl, ethyl, trifluoromethyl, difluoromethyl or trichloromethyl.

$R^{42}$ very particularly preferably represents hydrogen or methyl.

$R^{43}$ preferably represents hydrogen, fluorine, chlorine, bromine, iodine, cyano, methyl, ethyl, isopropyl or $C_1$-$C_2$-haloalkyl having 1 to 5 fluorine, chlorine and/or bromine atoms.

$R^{43}$ particularly preferably represents hydrogen, fluorine, chlorine, bromine, cyano, methyl, ethyl, isopropyl, trifluoromethyl, difluoromethyl, difluorochloromethyl or trichloromethyl.

$R^{43}$ very particularly preferably represents hydrogen, methyl, difluoromethyl or trifluoromethyl.

$R^{44}$ preferably represents hydrogen, fluorine, chlorine, bromine, methyl, ethyl or $C_1$-$C_2$-haloalkyl having 1 to 5 fluorine, chlorine and/or bromine atoms.

$R^{44}$ particularly preferably represents hydrogen, fluorine, chlorine, bromine, iodine, methyl or trifluoromethyl.

$R^{44}$ very particularly preferably represents hydrogen.

$R^{45}$ preferably represents methyl, ethyl, n-propyl or isopropyl.

$R^{45}$ particularly preferably represents methyl or ethyl.

Preference is given to those compounds of the formula (I) in which all radicals each have the meanings mentioned above as being preferred.

Particular preference is given to those compounds of the formula (I) in which all radicals each have the meanings mentioned above as being particularly preferred.

Preferred, and in each case to be understood as a sub-group of the compounds of the formula (I) mentioned above, are the following groups of novel carboxamides:

Group 1: Carboxamides of the formula (I-b)

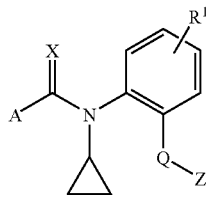
(I-b)

in which X, $R^1$, Q, Z and A are as defined above.

Group 2: Carboxamides of the formula (I-c)

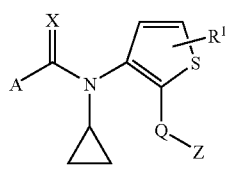
(I-c)

in which X, $R^1$, Q, Z and A are as defined above.

Group 3: Carboxamides of the formula (I-d)

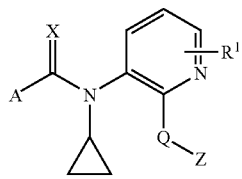
(I-d)

in which X, $R^1$, Q, Z and A are as defined above.

Group 4: Carboxamides of the formula (I-e)

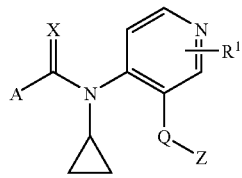
(I-e)

in which X, $R^1$, Q, Z and A are as defined above.

Group 5: Carboxamides of the formula (I-f)

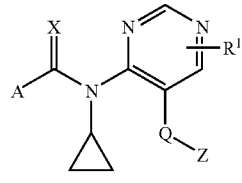
(I-f)

in which X, $R^1$, Q, Z and A are as defined above.

Group 6: Carboxamides of the formula (I-g)

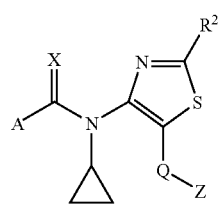
(I-g)

in which X, $R^2$, Q, Z and A are as defined above.

Group 7: 2-halofuryl/thienyl-3-carboxamides of the formula (I-h)

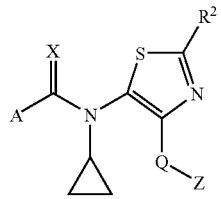

(I-h)

in which X, R², Q, Z and A are as defined above.

Preference is given to carboxamides of the formula (I) and of groups 1 to 7 in which Q represents a direct bond and Z represents $Z^1$.

Preference is given to carboxamides of the formula (I) and of groups 1 to 7 in which Q represents a direct bond and Z represents $Z^4$.

$Z^4$ especially preferably represents the grouping

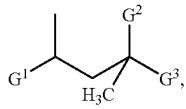

in which $G^1$ represents hydrogen or methyl, $G^2$ represents hydrogen or methyl, $G^3$ represents methyl or ethyl.

$Z^4$ also preferably represents one of the groupings G1 to G8

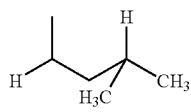
G1

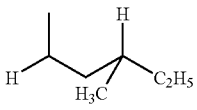
G2

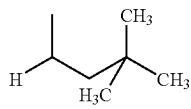
G3

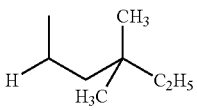
G4

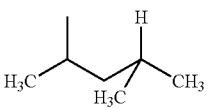
G5

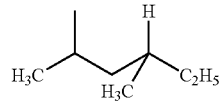
G6

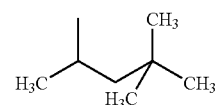
G7

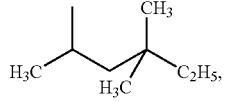
G8 particularly preferably G3, G5 or G7.

The definition $C_1$-$C_{20}$-alkyl comprises the largest range defined here for an alkyl radical. Specifically, this definition comprises the meanings methyl, ethyl, n-, isopropyl, n-, iso-, sec-, tert-butyl, and also in each case all isomeric pentyls, hexyls, heptyls, octyls, nonyls, decyls, undecyls, dodecyls, tridecyls, tetradecyls, pentadecyls, hexadecyls, heptadecyls, octadecyls, nonadecyls and eicosyls. A preferred range is $C_2$-$C_{12}$-alkyl, such as ethyl and straight-chain or branched propyl, butyl, pentyl, hexyl, heptyl, octyl, nonyl, decyl, undecyl and dodecyl, particularly straight-chain or branched $C_3$-$C_{10}$-alkyl, such as propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl, 2,6-dimethyl-4-heptyl and 1-methyl-2-cyclopropylethyl.

Halogen-substituted alkyl represents, for example, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

The substituent —$SiR^6R^7R^8$ preferably represents the following radicals: $SiMe_3$, $SiMe_2Et$, $SiMe_2CHMe_2$, SiMe$_2$CH$_2$CHMe$_2$, SiMe$_2$CH$_2$CMe$_3$, SiMe$_2$OCHMe$_2$, SiMe$_{20}$CH$_2$CHMe$_2$, SiMe$_2$OMe, SiMe$_2$CMe$_3$, SiMe$_2$CH$_2$CH$_2$Me.

The definition C$_2$-C$_{20}$-alkenyl comprises the largest range defined here for an alkenyl radical. Specifically, this definition comprises the meanings ethenyl, n-, isopropenyl, n-, iso-, sec-, tert-butenyl, and also in each case all isomeric pentenyls, hexenyls, heptenyls, octenyls, nonenyls, decenyls, undecenyls, dodecenyls, tridecenyls, tetradecenyls, pentadecenyls, hexadecenyls, heptadecenyls, octadecenyls, nonadecenyls and eicosenyls, 1-methyl-1-propenyl, 1-ethyl-1-butenyl, 2,4-dimethyl-1-pentenyl, 2,4-dimethyl-2-pentenyl.

The definition C$_2$-C$_{20}$-alkynyl comprises the largest range defined here for an alkynyl radical. Specifically, this definition comprises the meanings ethynyl, n-, isopropynyl, n-, iso-, sec-, tert-butynyl, and also in each case all isomeric pentynyls, hexynyls, heptynyls, octynyls, nonynyls, decynyls, undecynyls, dodecynyls, tridecynyls, tetradecynyls, pentadecynyls, hexadecynyls, heptadecynyls, octadecynyls, nonadecynyls and eicosynyls.

Optionally substituted radicals may be mono- or polysubstituted, where in the case of polysubstitution, the substituents may be identical or different. Thus, the definition dialkylamino also embraces an amino group which is substituted asymmetrically by alkyl, such as, for example, methylethylamino.

Halogen-substituted radicals, such as, for example, haloalkyl, are mono- or polyhalogenated. In the case of polyhalogenation, the halogen atoms may be identical or different. Here, halogen represents fluorine, chlorine, bromine and iodine, in particular fluorine, chlorine and bromine.

However, the general or preferred radical definitions or illustrations given above can also be combined with one another as desired, i.e. including combinations between the respective ranges and preferred ranges. They apply to the end products and, correspondingly, to precursors and intermediates.

Using, for example, 5-fluoro-1,3-dimethyl-1H-pyrazol-4-carbonyl chloride and 4'-chloro-N-cyclopropylbiphenyl-2-amine as starting materials and a base, the cause of the process (a) according to the invention can be illustrated by the reaction equation below:

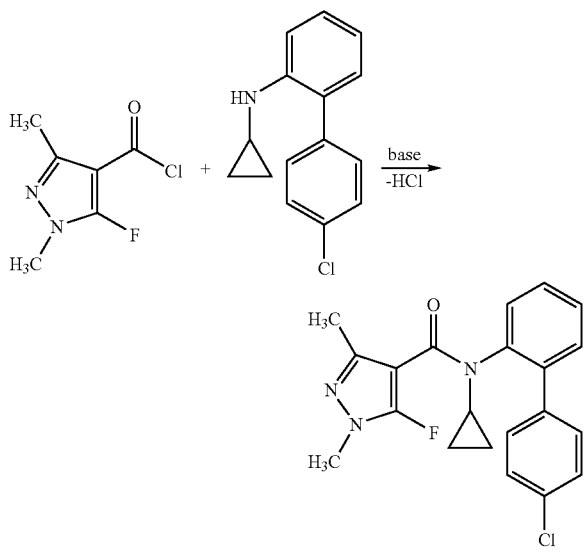

The formula (II) provides a general definition of the carbonyl halides required as starting materials for carrying out the process (a) according to the invention. In this formula (II), A and X preferably, particularly preferably, very particularly preferably and especially preferably have those meanings which have already been mentioned in connection with the description of the compounds of the formula (I) according to the invention as being preferred, particularly preferred, etc., for this radical. X$^1$ preferably represents fluorine, chlorine or hydroxyl, particularly preferably chlorine or hydroxyl.

The carbonyl halides of the formula (II) are known and/or can be prepared by known processes (cf., for example, EP-A 0 545 099, JP-A 01-290662 and U.S. Pat. No. 5,093,347).

The formula (III) provides a general definition of the cyclopropylamines furthermore required as starting materials for carrying out the process (a) according to the invention. In this formula (III), M, Q and Z preferably, particularly preferably, very particularly preferably and especially preferably have those meanings which have already been mentioned in connection with the description of the compounds of the formula (I) according to the invention as being preferred, particularly preferred, etc., for this radical.

The cyclopropylamines of the formula (III) are novel. They are obtained when (b) Amines of the formula (IV)

are reacted with cyclopropanone derivatives, such as, for example, their acetals or acetal derivatives, in particular mixed alkyl/silyl acetals, for example [(1-ethoxycyclopropyl)oxy](trimethyl)silane, in the presence of a reducing agent and, if appropriate, in the presence of an acid and a diluent.

The formula (IV) provides a general definition of the amines required as starting materials for carrying out the process (b) according to the invention. In this formula (IV), M, Q and Z preferably, particularly preferably, very particularly preferably and especially preferably have those meanings which have already been mentioned in connection with the description of the compounds of the formula (I) according to the invention as being preferred, particularly preferred, etc., for this radical.

The amines of the formula (V) are known (cf., for example, WO 03/070705, EP-A 0 824 099).

The cyclopropanone derivatives furthermore required as starting materials for carrying out the process (b) according to the invention, such as, for example, their acetals or acetal derivatives, are known chemicals for synthesis.

Suitable diluents for carrying out the process (a) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; their mixtures with water or pure water.

The process (a) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoholates, acetates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethyl-aniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (a) according to the invention is, if appropriate, carried out in the presence of a suitable coupling agent (if $X^5$ represents hydroxy). Suitable coupling agents are all customary carbonyl activators. These preferably include N-[3-(dimethylamino)propyl]-N'-ethyl-carbodiimide-hydrochloride, N,N'-di-sec-butylcarbodiimide, N,N'-dicyclohexylcarbodiimide, N,N'-diisopropylcarbodiimide, 1-(3-(dimethylamino)propyl)-3-ethylcarbodiimide methiodide, 2-bromo-3-ethyl-4-methylthiazolium tetrafluoroborate, N,N-bis[2-oxo-3-oxazolidinyl]phosphorodiamidic chloride, chlorotri-pyrrolidinophosphonium hexafluorophosphate, bromtripyrrolidinophosphonium hexafluorophosphate, O-(1H-benzotriazol-1-yloxy)tris(dimethylamino)phosphonium hexafluorophosphate, O-(1H-benzotriazol-1-yl)-N,N,N',N'-tetramethyluronium hexafluorophosphate, O-(1H-benzotriazol-1-yl)-N,N,N',N'-bis(tetramethylene)uronium hexafluorophosphate, O-(1H-benzotriazol-1-yl)-N,N,N',N'-bis-(tetramethylene)uronium tetrafluoroborate, N,N,N',N'-bis(tetramethylene)chlorouronium tetrafluoroborate, O-(7-azabenzotriazol-1-yl)-N,N,N,N-tetramethyluronium hexafluorophosphate and 1-hydroxybenzotriazole. These reagents can be employed separately, but also in combination.

When carrying out the process (a) according to the invention, the reaction temperatures can be varied within a relatively wide range. In general, the process is carried out at temperatures of from 0° C. to 150° C., preferably at temperatures of from 20° C. to 110° C.

For carrying out the process (a) according to the invention for preparing the compounds of the formula (I), in general from 0.2 to 5 mol, preferably from 0.5 to 2 mol, of cyclopropylamine of the formula (III) are employed per mole of the carbonyl halide of the formula (II). Work-up is carried out by customary methods.

Suitable diluents for carrying out the process (b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; ethers, such as diethyl ether, diisopropyl ether, methyl t-butyl ether, methyl t-amyl ether, dioxane, tetrahydrofuran, 1,2-dimethoxyethane, 1,2-diethoxyethane or anisols; nitriles, such as acetonitrile, propionitrile, n- or i-butyro-nitrile or benzonitrile; amides, such as N,N-dimethylformamide, N,N-dimethylacetamide, N-methyl-formanilide, N-methylpyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethandiol, propan-1,2-diol, ethoxyethanol, methoxyethanol, diethylene glycol monomethyl ether, diethylene glycol monoethyl ether, their mixtures with water or pure water.

When carrying out the process (b) according to the invention, the reaction temperatures can be varied within a relatively wide range. In general, the process is carried out at temperatures of from −40° C. to 150° C., preferably at temperatures of from 0° C. to 100° C.

If appropriate, the process (b) according to the invention is carried out in the presence of a suitable acid. Suitable acids are all customary inorganic or organic acids. Preference is given to using hydrochloric acid, sulphuric acid, hydrofluoric acid, phosphoric acid, p-toluenesulphonic acid, methanesulphonic acid, trifluoroacetic acid or trichloroacetic acid. Particular preference is given to using hydrochloric acid, sulphuric acid, p-toluenesulphonic acid or trifluoroacetic acid, very particularly preferably p-toluenesulphonic acid or acetic acid. If appropriate, the acid used can be employed as a mixture with water.

If appropriate, the process (b) according to the invention is carried out in the presence of a reducing agent. Suitable reducing agents are all customary inorganic or organic reducing agents. Preference is given to using metal hydrides, alkali metal or alkaline earth metal hydrides, and also their borohydrides, very particularly preferably sodium borohydride, sodium cyanoborohydride, lithium borohydride.

For carrying out the process (b) according to the invention for preparing the compounds of the formula (III), in general from 1 to 10 mol, preferably from 1 to 3 mol, of [(1-ethoxycyclopropyl)oxy](trimethyl)silane and from 1 to 100 mol, preferably from 1 to 10 mol, of reducing agent are employed per mole of the amine of the formula (IV). Work-up is carried out by customary methods.

The processes (a) and (b) according to the invention are generally carried out under atmospheric pressure. However, it is also possible to operate under elevated or reduced pressure-in general between 0.1 bar and 10 bar.

The compounds according to the invention exhibit a potent microbicidal activity and can be employed in plant protection and in the protection of materials for controlling undesirable microorganisms such as fungi and bacteria.

Fungicides can be employed in plant protection for controlling Plasmodiophoromycetes, Oomycetes, Chytridiomycetes, Zygomycetes, Ascomycetes, Basidiomycetes and Deuteromycetes.

Bactericides can be employed in plant protection for combating Pseudomonadaceae, Rhizobiaceae, Enterobacteriaceae, Corynebacteriaceae and Streptomycetaceae.

Examples which may be mentioned, but not by limitation, are some pathogens of fungal and bacterial diseases which come under the abovementioned general terms are:

diseases caused by powdery mildew pathogens, such as, for example

*Blumeria* species such as, for example, *Blumeria graminis;*

*Podosphaera* species such as, for example, *Podosphaera leucotricha;*

*Sphaerotheca* species such as, for example, *Sphaerotheca fuliginea;*

*Uncinula* species such as, for example, *Uncinula necator;* diseases caused by rust pathogens such as, for example,

*Gymnosporangium* species such as, for example, *Gymnosporangium sabinae*

*Hemileia* species such as, for example, *Hemileia vastatrix*;
*Phakopsora* species such as, for example, *Phakopsora pachyrhizi* and *Phakopsora meibomiae*;
*Puccinia* species such as, for example, *Puccinia recondita* or *Puccina graminis*;
*Uromyces* species such as, for example, *Uromyces appendiculatus*;

diseases caused by pathogens from the Oomycetene group such as, for example,
*Bremia* species such as, for example, *Bremia lactucae*;
*Peronospora* species such as, for example, *Peronospora pisi* or *P. brassicae*;
*Phytophthora* species such as, for example, *Phytophthora infestans*;
*Plasmopara* species such as, for example, *Plasmopara viticola*;
*Pseudoperonospora* species such as, for example, *Pseudoperonospora humuli* or *Pseudoperonospora cubensis*;
*Pythium* species such as, for example, *Pythium ultimum*;

leaf spot diseases and leaf wilts caused by, for example,
*Alternaria* species such as, for example, *Alternaria solani*;
*Cercospora* species such as, for example, *Cercospora beticola*;
*Cladosporum* species such as, for example, *Cladosporium cucumerinum*;
*Cochliobolus* species such as, for example, *Cochliobolus sativus (conidial form: Drechslera, syn: Helminthosporium)*;
*Colletotrichum* species such as, for example, *Colletotrichum lindemuthanium*;
*Cycloconium* species such as, for example, *Cycloconium oleaginum*;
*Diaporthe* species such as, for example, *Diaporthe citri*;
*Elsinoe* species such as, for example, *Elsinoe fawcettii*;
*Gloeosporium* species such as, for example, *Gloeosporium laeticolor*;
*Glomerella* species such as, for example, *Glomerella cingulata*;
*Guignardia* species such as, for example, *Guignardia bidwelli*;
*Leptosphaeria* species such as, for example, *Leptosphaeria maculans*;
*Magnaporthe* species such as, for example, *Magnaporthe grisea*;
*Mycosphaerella* species such as, for example, *Mycosphaerella graminicola* and *Mycosphaerella fijiensis*;
*Phaeosphaeria* species such as, for example, *Phaeosphaeria nodorum*;
*Pyrenophora* species such as, for example, *Pyrenophora teres*;
*Ramularia* species such as, for example, *Ramularia collocygni*;
*Rhynchosporium* species such as, for example, *Rhynchosporium secalis*;
*Septoria* species such as, for example, *Septoria apii*;
*Typhula* species such as, for example, *Typhula incamata*;
*Venturia* species such as, for example, *Venturia inaequalis*;

root and stem diseases caused by, for example,
*Corticium* species such as, for example, *Corticium graminearum*;
*Fusarium* species such as, for example, *Fusarium oxysporum*;
*Gaeumannomyces* species such as, for example, *Gaeumannomyces graminis*;
*Rhizoctonia* species such as, for example, *Rhizoctonia solani*;
*Tapesia* species such as, for example, *Tapesia acuformis* or *Tapesia yallundae*;

*Thielaviopsis* species such as, for example, *Thielaviopsis basicola*;

ear and panicle diseases (including maize cobs), caused by, for example,
i Alternaria species such as, for example, *Alternaria* spp.;
*Aspergillus* species such as, for example, *Aspergillus flavus*;
*Cladosporium* species such as, for example, *Cladosporium cladosporioides*;
*Claviceps* species such as, for example, *Claviceps purpurea*;
*Fusarium* species such as, for example, *Fusarium culmorum*;
*Gibberella* species such as, for example, *Gibberella zeae*;
*Monographella* species such as, for example, *Monographella nivalis*;

diseases caused by smuts such as, for example,
*Sphacelotheca* species such as, for example, *Sphacelotheca reiliana*;
*Tilletia* species such as, for example, *Tilletia caries*;
*Urocystis* species such as, for example, *Urocystis occulta*;
*Ustilago* species such as, for example, *Ustilago nuda*;

fruit rots caused by, for example,
*Aspergillus* species such as, for example, *Aspergillus flavus*;
*Botrytis* species such as, for example, *Botrytis cinerea*;
*Penicillium* species such as, for example, *Penicillium expansum* and *Penicillium purpurogenum*;
*Sclerotinia* species such as, for example, *Sclerotinia sclerotiorum*;
*Verticilium* species such as, for example, *Verticilium alboatrum*;

seed- and soil-borne rot and wilts, and seedling diseases, caused by, for example,
*Fusarium* species such as, for example, *Fusarium culmorum*;
*Phytophthora* species such as, for example, *Phytophthora cactorum*;
*Pythium* species such as, for example, *Pythium ultimum*;
*Rhizoctonia* species such as, for example, *Rhizoctonia solani*;
*Sclerotium* species such as, for example, *Sclerotium rolfsii*;

cancers, galls and witches' broom disease, caused by, for example,
*Nectria* species such as, for example, *Nectria galligena*;

wilts caused by, for example,
*Monilinia* species such as, for example, *Monilinia laxa*;

deformations of leaves, flowers and fruits, caused by, for example,
*Taphrina* species such as, for example, *Taphrina deformans*;

degenerative diseases of woody species, caused by, for example,
*Esca* species such as, for example, *Phaeomoniella clamydospora* and *Phaeoacremonium aleophilum* and *Fomitiporia mediterranea*;

diseases of flowers and seeds, caused by, for example,
*Botrytis* species such as, for example, *Botrytis cinerea*;

Diseases of the plant tubers, caused by, for example,
*Rhizoctonia* species such as, for example, *Rhizoctonia solani*;
*Helminthosporium* species such as, for example, *Helminthosporium solani*;

diseases caused by bacterial pathogens such as, for example,
*Xanthomonas* species such as, for example, *Xanthomonas campestris* pv. *oryzae*;

*Pseudomonas* species such as, for example, *Pseudomonas syringae* pv. *lachrymans*;

*Erwinia* species such as, for example, *Erwinia amylovora*.

The following diseases of soybeans can preferably be controlled:

Fungal diseases on leaves, stems, pods and seeds caused by, for example, alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*);

fungal diseases on roots and the stem base caused by, for example, black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also have a potent strengthening effect in plants. They are therefore suitable for mobilizing the plants' defences against attack by undesired microorganisms.

Plant-strengthening (resistance-inducing) substances are understood as meaning, in the present context, those substances which are capable of stimulating the defence system of plants in such a way that, when subsequently inoculated with undesired microorganisms, the treated plants display a substantial degree of resistance to these microorganisms.

In the present case, undesired microorganisms are understood as meaning phytopathogenic fungi, bacteria and viruses. Thus, the substances according to the invention can be employed for protecting plants against attack by the abovementioned pathogens within a certain period of time after the treatment. The period of time within which their protection is effected is generally extended from 1 to 28 days, preferably from 1 to 14 days, particularly preferably from 1 to 7 days, after the plants have been treated with the active compounds.

The fact that the active compounds, at the concentrations required for the controlling of plant diseases, are well tolerated by plants permits the treatment of aerial plant parts, of vegetative propagation material and seed, and of the soil.

In this context, the active compounds according to the invention can be employed particularly successfully for controlling cereal diseases such as, for example, against *Puccinia* species and of diseases in viticulture, fruit production and vegetable production such as, for example against *Botrytis, Venturia* or *Alternaria* species.

The active compounds according to the invention are also suitable for increasing the yield. Moreover, they display a low degree of toxicity and are well tolerated by plants.

If appropriate, the active compounds according to the invention can also be used in certain concentrations and application rates as herbicides, for influencing plant growth and for controlling animal pests. If appropriate, they can also be employed as intermediates and precursors for the synthesis of further active compounds.

All plants and plant parts can be treated in accordance with the invention. Plants are understood as meaning, in the present context, all plants and plant populations, such as desired and undesired wild plants or crop plants (including naturally occurring crop plants). Crop plants may be plants which can be obtained by conventional breeding and optimization methods or else by biotechnological and genetic engineering methods or by combinations of these methods, including the transgenic plants and including the plant varieties capable or not capable of being protected by Plant Breeders' rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example cuttings, tubers, rhizomes, slips and seeds.

The treatment according to the invention with the active compounds, of the plants and plant parts, is carried out directly or by acting on their environment, habitat, or store by the customary treatment methods, for example by immersion, spraying, vaporizing, fogging, broadcasting, painting on and, in the case of propagation material, in particular in the case of seeds, furthermore by coating with one or more coats.

In the protection of materials, the substances according to the invention can be employed for protecting industrial materials against attack and destruction by undesired microorganisms.

In the present context, industrial materials are understood as meaning non-live materials which have been made for use in technology. For example, industrial materials which are to be protected by active compounds according to the invention from microbial modification or destruction can be glues, sizes, paper and board, textiles, leather, timber, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, timber, paints, cooling lubricants and heat-transfer fluids, especially preferably wood.

Microorganisms which are capable of bringing about a degradation or modification of the industrial materials and which may be mentioned are, for example, bacteria, fungi, yeasts, algae and slime organisms. The active compounds according to the invention are preferably active against fungi, in particular moulds, wood-discolouring and wood-destroying fungi (Basidiomycetes) and against slime organisms and algae.

Examples which may be mentioned are microorganisms of the following genera:

*Alternaria* such as *Alternaria tenuis,*
*Aspergillus* such as *Aspergillus niger,*
*Chaetomium* such as *Chaetomium globosum,*
*Coniophora* such as *Coniophora puetana,*
*Lentinus* such as *Lentinus tigrinus,*
*Penicillium* such as *Penicillium glaucum,*
*Polyporus* such as *Polyporus versicolor,*
*Aureobasidium* such as *Aureobasidium pullulans,*
*Sclerophoma* such as *Sclerophoma pityophila,*
*Trichoderma* such as *Trichoderma viride,*
*Escherichia* such as *Escherichia coli,*
*Pseudomonas* such as *Pseudomonas aeruginosa,*
*Staphylococcus* such as *Staphylococcus aureus.*

Depending on their respective physical and/or chemical properties, the active compounds can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is, liquid solvents, pressurized liquefied gases and/or solid carriers, optionally with the use of surface-active agents, that is emulsifers and/or dispersants, and/or foam formers. If the extender used is water, it is also possible to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention, as such or in their formulations, can also be used as a mixture with known fungicides, bactericides, acaricides, nematicides, or insecticides, for example, to improve the activity spectrum or prevent the development of resistance. In many instances, synergistic effects are obtained, i.e. the activity of the mixture exceeds the activity of the individual components.

Examples of suitable co-components in mixtures are the following compounds:

Fungicides:
1) Nucleic acid synthesis inhibitors: for example benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;
2) mitosis and cell division inhibitors: for example benomyl, carbendazim, diethofencarb, ethaboxam, fuberidazole, pencycuron, thiabendazole, thiophanate-methyl, zoxamide;
3) respiration inhibitors (inhibitors of the respiratory chain):
3.1) inhibitors which act on complex I of the respiratory chain: for example diflumetorim;
3.2) inhibitors which act on complex II of the respiratory chain: for example boscalid/nicobifen, carboxin, fenfuram, flutolanil, furametpyr, furmecyclox, mepronil, oxycarboxin, penthiopyrad, thifluzamide;
3.3) inhibitors which act on complex III of the respiratory chain: for example amisulbrom, azoxystrobin, cyazofamid, dimoxystrobin, enestrobin, famoxadone, fenamidone, fluoxastrobin, kresoxim-methyl, meto-minostrobin, orysastrobin, picoxystrobin, pyraclostrobin, trifloxystrobin;
4) decouplers: for example dinocap, fluazinam, meptyldinocap;
5) ATP production inhibitors: for example fentin acetate, fentin chloride, fentin hydroxide, silthiofam;
6) amino acid and protein biosynthesis inhibitors: for example andoprim, blasticidin-S, cyprodinil, kasugamycin, kasugamycin hydrochloride hydrate, mepanipyrim, pyrimethanil;
7) signal transduction inhibitors: for example fenpiclonil, fludioxonil, quinoxyfen;
8) lipid and membrane synthesis inhibitors: for example biphenyl, chlozolinate, edifenphos, iodocarb, iprobenfos, iprodione, isoprothiolane, procymidone, propamocarb, propamocarb hydrochloride, pyrazophos, tolclofos-methyl, vinclozolin;
9) ergosterol biosynthesis inhibitors: for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

10) cell wall synthesis inhibitors: for example benthiavalicarb, dimethomorph, flumorph, iprovalicarb, polyoxins, polyoxorim, validamycin A;

11) melanin biosynthesis inhibitors: for example carpropamid, diclocymet, fenoxanil, phthalide, pyroquilon, tricyclazole;

12) resistance inductors: for example acibenzolar-S-methyl, probenazole, tiadinil;

13) compounds with multi-site activity: for example Bordeaux mixture, captafol, captan, chlorothalonil, copper naphthenate, copper oxide, copper oxychloride, copper preparations such as, for example, copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations such as, for example, calcium polysulphide, thiram, tolylfluanid, zineb, ziram;

14) a compound selected from the following enumeration: N-methyl-(2E)-2-(2-{[6-(3-chloro-2-methylphenoxy)-5-fluoropyrimidin-4-yl]oxy}phenyl)-2-(methoxyimino)acetamide, N-methyl-(2E)-2-{2-[({[(1E)-1-(3-{[(E)-1-fluoro-2-phenylvinyl]oxy}phenyl)ethylidene]amino}oxy)methyl]phenyl}-2-(methoxyimino) acetamide, 1-(4-chlorophenyl)-2-(1H-1,2,4-triazol-1-yl) cycloheptanol, 1-[(4-methoxyphenoxy)methyl]-2,2-dimethylpropyl-H-imidazole-1-carboxylate, 2-(4-chlorophenyl)-N-{2-[3-methoxy-4-(prop-2-yn-1-yloxy) phenyl]ethyl}-2-(prop-2-yn-1-yloxy)acetamide, 2,3,5,6-tetrachloro-4-(methylsulphonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts thereof, 3,4,5-trichloropyridine-2,6-dicarbonitrile, 3,4-dichloro-N-(2-cyanophenyl) isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4] triazolo[1,5-a]pyrimidine-7-amine, 5-chloro-7-(4-methylpiperidin-1-yl)-6-(2,4,6-trifluorophenyl)[1,2,4] triazolo[1,5-a]pyrimidine, 5-chloro-N-[(1R)-1,2-dimethylpropyl]-6-(2,4,6-trifluorophenyl)[1,2,4]triazolo [1,5-a]pyrimidine-7-amine, 8-hydroxyquinoline sulphate, benthiazole, bethoxazin, capsimycin, carvone, quinomethionate, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulphamide, fosetyl-aluminium, fosetyl-calcium, fosetyl-sodium, hexachlorobenzene, irumamycin, methasulphocarb, methyl (2-chloro-5-{(1E)-N-[(6-methylpyridin-2-yl)methoxy]ethanimidoyl}benzyl)carbamate, methyl (2E)-2-{2-[({cyclopropyl[(4-methoxyphenyl) imino]methyl}thio)methyl]phenyl}-3-methoxyacrylate, methyl 1-(2,2-dimethyl-2,3-dihydro-1H-inden-1-yl)-1H-imidazole-5-carboxylate, methyl 3-(4-chlorophenyl)-3-{ [N-(isopropoxycarbonyl)valyl]amino}propanoate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulphonamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl) ethyl]-2-fluoro-4-iodonicotinamide, N-[2-(4-{[3-(4-chlorophenyl)prop-2-yn-1-yl]oxy}-3-methoxyphenyl)ethyl]-$N^2$-(methylsulphonyl)valinamide, N-{(Z)-[(cyclopropylmethoxy)imino][6-(difluoromethoxy)-2,3-difluorophenyl]methyl}-2-phenylacetamide, N-{2-[3-chloro-5-(trifluoromethyl)pyridin-2-yl]ethyl}-2-(trifluoromethyl)benzamide, natamycin, nickel dimethyl dithiocarbamate, nitrothal-isopropyl, O-{1-[(4-methoxyphenoxy)methyl]-2,2-dimethylpropyl} 1H-imidazole-1-carbothioate, octhilinone, oxamocarb, oxyfenthiin, pentachlorophenol and salts, phosphoric acid and its salts, piperalin, propamocarb fosetylate, propanosine-sodium, proquinazid, pyrrolnitrine, quintozene, tecloftalam, tecnazene, triazoxide, trichlamide, zarilamid.

Bactericides:

Bronopol, dichlorophen, nitrapyrin, nickel dimethyl dithiocarbamate, kasugamycin, octhilinone, furan-carboxylic acid, oxytetracyclin, probenazole, streptomycin, tecloftalam, copper sulphate and other copper preparations.

Insecticides/Acaricides/Nematicides:

1. Acetylcholine Esterase (AChE) Inhibitors 1.1 Carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbo-sulphan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)

1.2 Organophosphates (for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fos-methilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion)

2. Sodium Channel Modulators/Voltage-Dependent Sodium Channel Blockers 2.1 Pyrethroids (for example acrinathrin, allethrin (d-cis-trans, d-trans), beta-cyfluthrin, bifenthrin, bio-allethrin, bio-allethrin-S-cyclopentyl isomer, bioethanomethrin, biopermethrin, bioresmethrin, chlo-vaporthrin, cis-cypermethrin, cis-resmethrin, cis-permethrin, clocythrin, cyprothrin, cyfluthrin, cyhalothrin, cypermethrin (alpha-, beta-, theta-, zeta-), cyphenothrin, DDT, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, pennethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum))

2.2 Oxadiazines (for example indoxacarb)

3. Acetylcholine Receptor Agonists/Antagonists 3.1 Chloronicotinyls/neonicotinoids (for example acetamiprid, clothianidin, dinotefuran, imidacloprid, ni-tenpyram, nithiazine, thiacloprid, thiamethoxam)

3.2 Nicotine, bensultap, cartap

4. Acetylcholine Receptor Modulators 4.1 Spinosyns (for example spinosad)

5. GABA-Controlled Chloride Channel Antagonists 5.1 Cyclodiene organochlorines (for example camphechlor, chlordane, endosulphan, gamma-HCH, HCH, heptachlor, lindane, methoxychlor 5.2 Fiprole (for example acetoprole, ethiprole, fipronil, vaniliprole)

6. Chloride Channel Activators 6.1 Mectins (for example abamectin, avermectin, emamectin, emamectin benzoate, ivermectin, milbemectin, milbemycin)

7. Juvenile Hormone Mimetics (for example diofenolan, epofenonane, fenoxycarb, hydroprene, kinoprene, methoprene, pyriproxifen, triprene)

8. Ecdysone Agonists/Disruptors 8.1 Diacylhydrazines (for example chromafenozide, halofenozide, methoxyfenozide, tebufenozide)

9. Chitin Biosynthesis Inhibitors 9.1 Benzoylureas (for example bistrifluoron, chlofluazuron, diflubenzuron, fluazuron, flucycloxuron, flu-fenoxuron, hexaflumuron, lufenuron, novaluron, noviflumuron, penfluoron, teflubenzuron, triflumuron)

9.2 Buprofezin 9.3 Cyromazine

10. Inhibitors of Oxidative Phosphorylation, ATP Disruptors 10.1 Diafenthiuron 10.2 Organotins (for example azocyclotin, cyhexatin, fenbutatin oxides)

11. Uncouplers of oxidative phosphorylation by interrupting the H-proton gradient 11.1 Pyrroles (for example chlorfenapyr)

11.2 Dinitrophenols (for example binapacyrl, dinobuton, dinocap, DNOC)

12. Site-I Electron Transport Inhibitors 12.1 METIs (for example fenazaquin, fenpyroximate, pyrimidifen, pyridaben, tebufenpyrad, tolfenpyrad)

12.2 Hydramethylnon 12.3 Dicofol

13. Site-II Electron Transport Inhibitors 13.1 Rotenone

14. Site-III Electron Transport Inhibitors 14.1 Acequinocyl, fluacrypyrim 15. Microbial Disruptors of the Insect Gut Membrane

*Bacillus thuringiensis* strains

16. Fat Synthesis Inhibitors 16.1 Tetronic acids (for example spirodiclofen, spiromesifen)

16.2 Tetramic acids [for example 3-(2,5-dimethylphenyl)-8-methoxy-2-oxo-1-azaspiro[4.5]dec-3-en-4-yl ethyl carbonate (also known as: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS Reg. No.: 203313-25-1)]

17. Carboxamides (for example flonicamid)

18. Octopaminergic Agonists (for example amitraz)

19. Inhibitors of Magnesium-Stimulated ATPase (for example propargite)

20. Agonists of the Ryanodin Receptor 20.1 Benzoic acid dicarboxamides (for example $N^2$-[1,1-dimethyl-2-(methylsulphonyl)ethyl]-3-iodo-N'-[2-methyl-4-[1,2,2,2-tetrafluoro-1-(trifluoromethyl)ethyl]phenyl]-1,2-benzenedicarboxamide (CAS Reg.-No.: 272451-65-7), flubendiamide)

20.2 Anthranilamides (for example DPX E2Y45=3-bromo-N-{4-chloro-2-methyl-6-[(methylamino)carbonyl]-phenyl}-1-(3-chloropyridin-2-yl)-1H-pyrazol-5-carboxamide)

21. Nereistoxin Analogues (for example thiocyclam hydrogen oxalate, thiosultap sodium)

22. Biologicals, Hormones or Pheromones (for example azadirachtin, *Bacillus* spec., *Beauveria* spec., codlemone, *Metarrhizium* spec., *Paecilomyces* spec., thuringiensin, *Verticillium* spec.)

23. Active Compounds with Unknown or Unspecific Mechanisms of Action 23.1 Fumigants (for example aluminium phosphide, methyl bromide, sulphuryl fluoride)

23.2 Selective antifeedants (for example cryolite, flonicamid, pymetrozine)

23.3 Mite growth inhibitors (for example clofentezine, etoxazole, hexythiazox)

23.4 Amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulphluramid, tetradifon, tetrasul, triarathene, verbutin, furthermore the compound 3-methyl-phenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomers (CAS Reg. No. 185984-60-5) (cf. WO 96/37494, WO 98/25923), and preparations which contain insecticidally active plant extracts, nematodes, fungi or viruses.

A mixture with other known active compounds such as herbicides, or with fertilizers and growth regulators, safeners or semiochemicals is also possible.

In addition, the compounds of the formula (I) according to the invention also have very good antimycotic activity. They have a very broad antimycotic spectrum of action, in particular against dermatophytes and budding fungi, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The enumeration of these fungi is no restriction whatsoever of the mycotic spectrum which can be controlled and is provided by illustration only.

The active compounds can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, broadcasting, dusting, foaming, painting on and the like. It is furthermore possible to apply the active compounds by the ultra-low-volume method, or to inject the active compound preparation or the active compound itself into the soil. The seed of the plants can also be treated.

When employing the active compounds according to the invention as fungicides, the application rates can be varied within a substantial range, depending on the type of application. In the treatment of plant parts, the application rates of active compound are generally between 0.1 and 10 000 g/ha, preferably between 10 and 1000 g/ha. For the treatment of seed, the application rates of active compound are generally between 0.001 and 50 g per kilogram of seed, preferably between 0.01 and 10 g per kilogram of seed. For treating the soil, the application rates of active compound are generally between 0.1 and 10 000 g/ha, preferably between 1 and 5000 g/ha.

As already mentioned above, all plants and their parts can be treated in accordance with the invention. In a preferred embodiment, plant species and plant cultivars which are found in the wild or are obtained by traditional biological breeding methods, such as hybridization or protoplast fusion, and parts of the former are treated. In a further preferred embodiment, transgenic plants and plant cultivars which have been obtained by recombinant methods, if appropriate in combination with traditional methods (genetically modified organisms) and their parts are treated. The term "parts" or "parts of plants" or "plant parts" has been illustrated above.

Particularly preferably, plants of the plant cultivars which are in each case commercially available or in use are treated according to the invention. Plant cultivars are understood as meaning plants with new properties ("traits") which have been obtained by conventional cultivation, by mutagenesis or else by recombinant DNA techniques. These may be cultivars, breeds, biotypes or genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or extensions of the activity spectrum and/or an increase in the activity of the substances and compositions that can be used according to the invention, better plant growth, more developed root system, higher resistance of the plant species or plant cultivar, increased growth of shoots, higher plant vitality, increased tolerance to high or low temperatures, increased tolerance to drought or to water or soil salinity, increased flowering performance, easier harvesting, accelerated maturation, higher harvest yields, larger fruit, increased plant size, greener leaf colour, earlier blossoming, better quality and/or a higher nutritional value of the harvested products, higher sugar concentration in the fruits, better storage stability and/or processability of the harvested products which exceed the effects which were actually to be expected are possible.

The preferred transgenic plants or plant cultivars (i.e. those obtained by genetic engineering) which are to be treated according to the invention include all plants which, as a result of the recombinant modification, received genetic material which imparts particularly advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes, slugs and snails as the result of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also particularly emphasized are the increased defence of plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosates, for example maize, cotton, soya beans), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

PREPARATION EXAMPLES

Preparation of compound No. 3

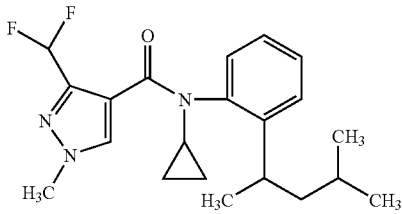

At room temperature, 70 μl (0.8 mmol) of oxal chloride and 30 μl of dimethylformamide are added to a suspension consisting of 130.0 mg (0.7 mmol) of 3-(difluoromethyl)-1-methyl-1H-pyrazol-4-carboxylic acid in 5 ml of dichloromethane. After 2 hours, this reaction mixture is added dropwise to a solution consisting of 160.0 mg (0.7 mmol) of N-cyclopropyl-2-(1,3-dimethylbutyl)aniline and 130 μl (1.0 mmol) of triethylamine in 5 ml of dichloromethane. After 48 hours of stirring at room temperature, 4 ml of water are added and the organic phase is separated off, dried over magnesium sulphate and concentrated under reduced pressure. This gives, after column chromatography (gradient cyclohexane/ethyl acetate), 202.0 mg (0.5 mmol, 72% of theory) of N-cyclopropyl-3-(difluoromethyl)-N-[2-(1,3-dimethylbutyl)phenyl]-1-methyl-1H-pyrazol-4-carboxamide [log P (pH 2.3) 3.89].

Analogously to this example and in accordance with the general descriptions of the processes according to the invention, it is possible to obtain the compounds of the formula (I) mentioned in Table 1 below.

TABLE 1

(I)

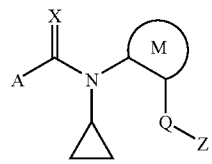

| No. | X | M | Q | Z | A | logP (pH 2.3) |
|---|---|---|---|---|---|---|
| 1 | O | M-1, R¹ = H | direct bond | G5 | 3-CF₃, 4-CH₃, 1-CH₃ pyrazole | |
| 2 | O | M-1, R¹ = H | direct bond | G5 | 3-CH₃, 4-CH₃, 5-F, 1-CH₃ pyrazole | 3.74 |
| 3 | O | M-1, R¹ = H | direct bond | G5 | 3-CHF₂, 4-CH₃, 1-CH₃ pyrazole | 3.89 |
| 4 | O | M-1, R¹ = H | direct bond | G5 | 3-methyl-2-chloropyridine | |

TABLE 1-continued
(I)
| No. | X | M | Q | Z | A | logP (pH 2.3) |
|---|---|---|---|---|---|---|
| 5 | O | M-1, R¹ = H | direct bond | 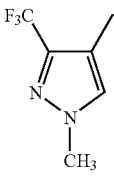 | 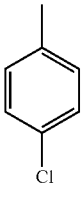 | |
| 6 | O | M-1, R¹ = H | direct bond | 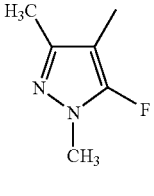 | 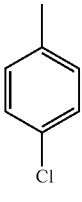 | 3.22 |
| 7 | O | M-1, R¹ = H | direct bond | 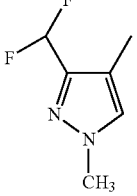 |  | 3.38 |
| 8 | O | M-1, R¹ = H | direct bond | 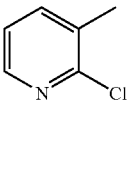 | 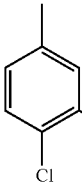 | |
| 9 | O | M-1, R¹ = 4-F | direct bond | 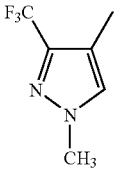 | 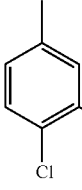 | |
| 10 | O | M-1, R¹ = 4-F | direct bond | 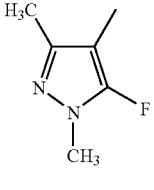 | | 3.74 |

TABLE 1-continued (I)

| No. | X | M | Q | Z | A | logP (pH 2.3) |
|-----|---|---|---|---|---|---------------|
| 11 | O | M-1, R¹ = 4-F | direct bond | | 3,4-dichlorophenyl | 3-difluoromethyl-4-methyl-1-methyl-pyrazol-5-yl | 3.85 |
| 12 | O | M-1, R¹ = 4-F | direct bond | | 3,4-dichlorophenyl | 2-chloro-3-methyl-pyridin-... | |
| 13 | O | M-2, R¹ = H | direct bond | G5 | 3-trifluoromethyl-4-methyl-1-methyl-pyrazol-5-yl | |
| 14 | O | M-2, R¹ = H | direct bond | G5 | 3-methyl-4-methyl-5-fluoro-1-methyl-pyrazol-... | |
| 15 | O | M-2, R¹ = H | direct bond | G5 | 3-difluoromethyl-4-methyl-1-methyl-pyrazol-5-yl | |
| 16 | O | M-2, R¹ = H | direct bond | G5 | 2-chloro-3-methyl-pyridin-... | |

Preparation of Starting Materials of the Formula (III)

Example (III-1)

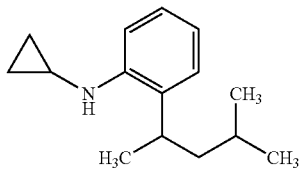

At room temperature, 1.7 ml (30.0 mmol) of acetic acid and 627.5 mg (3.6 mmol) of [(1-ethoxycyclopropyl)oxy](trimethyl)silane are added to a solution consisting of 531.9 mg (3.0 mmol) of 2-(1,3-dimethylbutyl)aniline in 5 ml of methanol over 1.0 g of 3 Å molecular sieve. The reaction mixture is stirred at room temperature for 20 minutes, and 1.04 g (16.5 mmol) of sodium cyanoborohydride are then added. The reaction mixture is stirred at 50° C. for 16 hours. At room temperature, 10 ml of water are added. The reaction mixture is filtered and the filtrate is concentrated. 10 ml of 1 mol/l aqueous sodium hydroxide solution are added to the residue, and the mixture is extracted 3 times with in each case 20 ml of diethyl ether. The organic phase is washed with saturated sodium chloride solution, dried over sodium sulphate and concentrated under reduced pressure. This gives, after column chromatography (gradient cyclohexane/ethyl acetate), 220.0 mg (1.0 mmol, 34% of theory) of N-cyclopropyl-2-(1,3-dimethylbutyl)aniline [log P (pH 2.3) 5.33].

Analogously to example (III-1) and in accordance with the general descriptions of the processes according to the invention, it is possible to obtain the compounds of the formula (III) mentioned in Table 2 below.

TABLE 2

(III)

| No. | M | Q | Z | logP (pH 2.3) |
|---|---|---|---|---|
| III-1 | M-1, $R^1$ = H | direct bond | G5 | 5.33 |
| III-2 | M-1, $R^1$ = H | direct bond | 4-Cl-phenyl | 4.99 |
| III-3 | M-1, $R^1$ = 4-F | direct bond | 3,4-diCl-phenyl | 5.46 |

The log P values given in the Tables and Preparation Examples above are determined in accordance with EEC Directive 79/831 Annex V.A8 by HPLC (High Performance Liquid Chromatography) on a reversed-phase column (C 18). Temperature: 43° C.

The determination is carried out in the acidic range at pH 2.3 using the mobile phases 0.1% aqueous phosphoric acid and acetonitrile; linear gradient from 10% acetonitrile to 90% acetonitrile.

Calibration is carried out using unbranched alkan-2-ones (having 3 to 16 carbon atoms) with known log P values (determination of the log P values by the retention times using linear interpolation between two successive alkanones).

The lambda max values were determined in the maxima of the chromatographic signals using the UV spectra from 200 nm to 400 nm.

Use Examples

Example A

| Uromyces test (bean)/protective | |
|---|---|
| Solvents: | 24.5 parts by weight of acetone |
|  | 24.5 parts by weight of dimethylacetamide |
| Emulsifier: | 1 part by weight of alkylaryl polyglycol ether |

To produce a suitable preparation of active compound, 1 part by weight of active compound is mixed within the stated amounts of solvents and emulsifier and the concentrate is diluted with water to the desired concentration.

To test for protective activity, the young plants are sprayed with the active compound preparation at the stated application rate. After the spray coating has dried on, the plants are inoculated with an aqueous spore suspension of the bean rust pathogen Uromyces appendiculatus and then remain in an incubation cabin at about 20° C. and 100% relative atmospheric humidity for 1 day. The plants are then placed in a greenhouse at about 21° C. and a relative atmospheric humidity of about 90%.

Evaluation is carried out 10 days after the inoculation. 0% means an efficiency which corresponds to that of the control, whereas an efficacy of 100% means that no infection is observed.

TABLE A

| Active compound according to the invention | Application rate of active compound in ppm | Efficacy in % |
|---|---|---|
| *Uromyces* test (bean)/protective | | |
| (2) 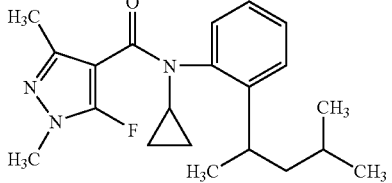 | 100 | 100 |
| (3) 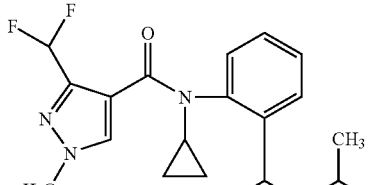 | 100 | 100 |
| (6) 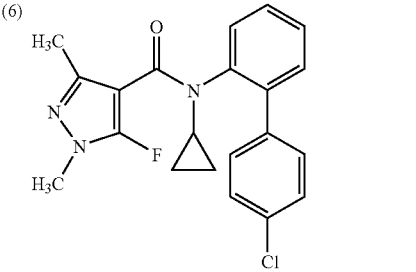 | 100 | 93 |

Example B

| *Alternaria* test (tomato)/protective | |
|---|---|
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier and the concentrate is diluted with water to the desired concentration.

To test for protective activity, young tomato plants are sprayed with the active compound preparation at the stated application rate. 1 day after the treatment, the plants are inoculated with a spore suspension of *Alternaria solani* and then remain at 100% relative atmospheric humidity and 20° C. for 24 h. The plants then remain at 96% relative atmospheric humidity and a temperature of 20° C.

Evaluation is carried out 7 days after the inoculation. 0% means an efficacy which corresponds to that of the control, whereas an efficacy of 100% means that no infection is observed.

TABLE B

| Active compound according to the invention | Application rate of active compound in ppm | Efficacy in % |
|---|---|---|
| *Alternaria* test (tomato)/protective | | |
| (2) 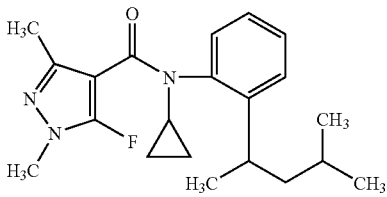 | 1000 | 100 |

TABLE B-continued

Alternaria test (tomato)/protective

| Active compound according to the invention | Application rate of active compound in ppm | Efficacy in % |
|---|---|---|
| (3) [structure] | 1000 | 94 |
| (7) [structure] | 1000 | 89 |
| (10) [structure] | 1000 | 89 |
| (11) [structure] | 1000 | 94 |

Example C

| Pyrenophora teres test (barley)/protective | |
|---|---|
| Solvent: | 50 parts by weight of N,N-dimethylacetamide |
| Emulsifier: | 1 part by weight of alkylaryl polyglycol ether |

To produce a suitable preparation of active compound, 1 part by weight of active compound is mixed with the stated amounts of solvent and emulsifier and the concentrate is diluted with water to the desired concentration.

To test for protective activity, young plants are sprayed with the active compound preparation at the stated application rate. After the spray coating has dried on, the plants are sprayed with a conidia suspension of *Pyrenophora teres*. The plants remain in an incubation cabin at 20° C. and 100% relative atmospheric humidity for 48 hours.

The plants are then placed in a greenhouse at a temperature of about 20° C. and a relative atmospheric humidity of about 80%.

Evaluation is carried out 8 days after the inoculation. 0% means an efficacy which corresponds to that of the control, whereas an efficacy of 100% means that no infection is observed.

TABLE C

*Pyrenophora teres* test (barley)/protective

| Active compound according to the invention | Application rate of active compound in ppm | Efficacy in % |
|---|---|---|
| (6) ![structure] | 500 | 80 |
| (7) ![structure] | 500 | 95 |
| (10) ![structure] | 500 | 95 |

The invention claimed is:

1. Carboxamide of formula (I)

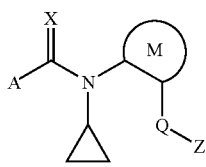

in which

X represents O (oxygen) or S (sulphur),

M represents a phenyl, thiophene, pyridine, pyrimidine, pyridazine or pyrazine ring, each of which is monosubstituted by $R^1$, or represents a thiazol ring which is substituted by $R^2$, $R^1$ represents hydrogen, fluorine, chlorine, methyl isopropyl, methylthio or trifluoromethyl, $R^2$ represents hydrogen, methyl, methylthio or trifluoromethyl, Q represents a direct bond, $C_1$-$C_4$-alkylene, $C_2$-$C_4$-alkenylene, O, S, SO, $SO_2$ or $NR^3$, $R^3$ represents hydrogen, $C_1$-$C_8$-alkyl, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-halogenalkyl, $C_2$-$C_6$-halogenalkenyl, $C_2$-$C_6$-halogenalkynyl or $C_3$-$C_6$-cycloalkyl, Z represents $Z^1$, $Z^2$, $Z^3$, $Z^4$, $Z^5$ or $Z^6$, $Z^1$ represents a phenyl which is optionally mono- to pentasubstituted by identical or different substituents, $Z^2$ represents pyridinyl which is optionally mono- to trisubstituted by identical or different substituents, $Z^3$ represents cycloalkyl or bicycloalkyl, each of which is optionally mono- or polysubstituted by identical or different substituents from the group consisting of halogen, alkyl and/or —$(CR^4R^5)_m SiR^6R^7R^8$, $Z^4$ represents unsubstituted $C_2$-$C_{20}$-alkyl or represents $C_1$-$C_{20}$-alkyl which is mono- or polysubstituted by identical or different substituents from the group consisting of halogen, alkylthio, alkylsulphinyl, alkylsulphonyl, alkoxy, alkylamino, dialkylamino, halogenalkylthio, halogenalkylsulphinyl, halogenalkylsulphonyl, halogenalkoxy, halogenalkylamino, halogen-dialkylamino, —$SiR^6R^7R^8$ and $C_3$-$C_6$-cycloalkyl, where the cycloalkyl moiety for its part may optionally be mono- or polysubstituted by identical or different substituents from the group consisting of halogen and $C_1$-$C_4$-alkyl, $Z^5$ represents $C_2$-$C_{20}$-alkenyl or $C_2$-$C_{20}$-alkynyl, each of which is optionally mono- or polysubstituted by identical or different substituents from the group consisting of halogen, alkylthio, alkylsulphinyl, alkylsulphonyl, alkoxy, alkylamino, dialkylamino, halogenalkylthio, halogenalkylsulphinyl, halogenalkylsulphonyl, halogenalkoxy, halogenalkylamino, halogen-dialkylamino, —$SiR^6R^7R^8$ and $C_3$-$C_6$-cycloalkyl, where the cycloalkyl moiety for its part may optionally be mono- or polysubstituted by identical or different substituents from the group consisting of halogen and $C_1$-$C_4$-alkyl, $Z^6$ represents a saturated or unsaturated 3- to 7-membered ring which is optionally mono- or polysubstituted and which contains a silicon atom as ring member, in which case Q represents a direct bond or $C_1$-$C_4$-alkylene, $R^4$ represents hydrogen or $C_1$-$C_4$-alkyl, $R^5$ represents hydrogen or $C_1$-$C_4$-alkyl, m represents 0, 1, 2 or 3, $R^6$ and $R^7$ independently of one another represent hydrogen, $C_1$-$C_8$alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-halogenalkyl, $R^8$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$alkynyl, $C_1$-$C_6$-halogenalkyl, $C_2$-$C_6$-halogenalkenyl, $C_2$-$C_6$-halogenalkynyl, $C_3$-$C_6$-cycloalkyl, or represents in each case optionally substituted phenyl or phenylalkyl, or M-Q-Z together represent 1H-2,3-dihydro-inden-4-yl, 1,3-dihydro-2-benzofuran-4-yl or 1,3-dihydro-2-benzothien-4-yl, each of which is optionally mono- to trisubstituted by methyl, A represents one of the radicals A1 to A19 below

A1

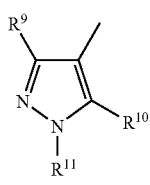

A2

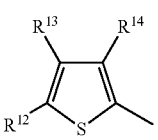

A3

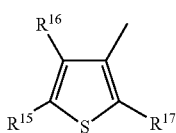

A4

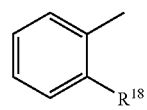

A5

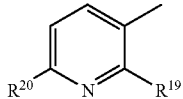

-continued

A6

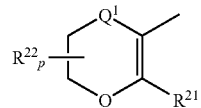

A7

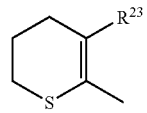

A8

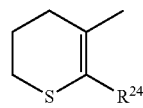

A9

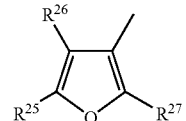

A10

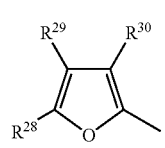

A11

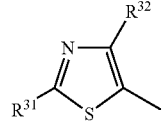

A12

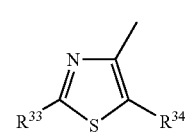

A13

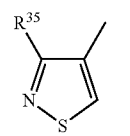

A14

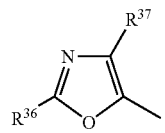

A15

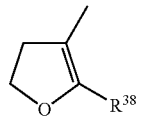

A16

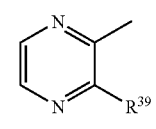

A17

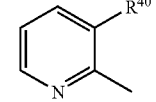

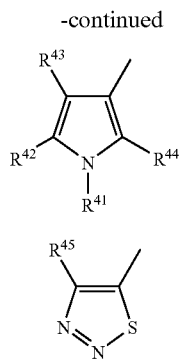

R⁹ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-halogenalkyl, $C_1$-$C_4$halogenalkoxy or $C_1$-$C_4$-halogenalkylthio having in each case 1 to 5 halogen atoms, aminocarbonyl or aminocarbonyl-$C_1$-$C_4$-alkyl, $R^{10}$ represents hydrogen, halogen, cyano, $C_1$-$C_4$-alkyl, $C_1$-$C_4$-alkoxy or $C_1$-$C_4$-alkylthio, $R^{11}$ represents hydrogen, $C_1$-$C_4$-alkyl, hydroxy-$C_1$-$C_4$-alkyl,$C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$C_4$-alkyl, $C_1$-$C_4$-halogenalkyl, $C_1$-$C_4$-halogenalkylthio-$C_1$-$C_4$-alkyl, $C_1$-$C_4$halogenalkoxy-$C_1$-$C_4$-alkyl having in each case 1 to 5 halogen atoms, or phenyl, $R^{12}$ and $R^{13}$ independently of one another represent hydrogen, halogen, $C_1$-$C_4$-alkyl or $C_1$-$C_4$-halogenalkyl having 1 to 5 halogen atoms, $R^{14}$ represents halogen, cyano or $C_1$-$C_4$-alkyl, or $C_1$-$C_4$halogenalkyl or $C_1$-$C_4$-halogenalkoxy having in each case 1 to 5 halogen atoms, $R^{15}$ and $R^{16}$ independently of one another represent hydrogen, halogen, $C_1$-$C_4$-alkyl or $C_1$-$C_4$-halogenalkyl having 1 to 5 halogen atoms, $R^{17}$ represents hydrogen, halogen, $C_1$-$C_4$-alkyl or $C_1$-$C_4$halogenalkyl having 1 to 5 halogen atoms, $R^{18}$ represents hydrogen, halogen, hydroxy, cyano, $C_1$-$C_6$-alkyl, $C_1$-$C_4$-halogenalkyl, $C_1$-$C_4$-halogenalkoxy or $C_1$-$C_4$-halogenalkylthio having in each case 1 to 5 halogen atoms, $R^{19}$ represents halogen, hydroxy, cyano, $C_1$-$C_4$-alkyl, $C_1$-$C_4$-alkoxy, $C_1$-$C_4$-alkylthio, $C_1$-$C_4$-halogenalkyl, $C_1$-$C_4$-halogenalkylthio or $C_1$-$C_4$halogenalkoxy having in each case 1 to 5 halogen atoms, $R^{20}$ represents hydrogen, halogen, cyano, $C_1$-$C_4$-alkyl, $C_1$-$C_4$-alkoxy, $C_1$-$C_4$-alkylthio, $C_1$-$C_4$-halogenalkyl, $C_1$-$C_4$-halogenalkoxy having in each case 1 to 5 halogen atoms, $C_1$-$C_4$-alkylsulphinyl or $C_1$-$C_4$-alkylsulphonyl, $R^{21}$ represents $C_1$-$C_4$-alkyl or $C_1$-$C_4$-halogenalkyl having 1 to 5 halogen atoms, $R^{22}$ represents $C_1$-$C_4$-alkyl, $Q^1$ represents S (sulphur), SO, $SO_2$ or $CH_2$, p represents 0, 1 or 2, where $R^{22}$ represents identical or different radicals if p represents 2, $R^{23}$ represents $C_1$-$C_4$-alkyl or $C_1$-$C_4$-halogenalkyl having 1 to 5 halogen atoms, $R^{24}$ represents $C_1$-$C_4$-alkyl or $C_1$-$C_4$-halogenalkyl having 1 to 5 halogen atoms, $R^{25}$ and $R^{26}$ independently of one another represent hydrogen, halogen, amino, $C_1$-$C_4$-alkyl or $C_1$-$C_4$-halogenalkyl having 1 to 5 halogen atoms, $R^{27}$ represents hydrogen, halogen, $C_1$-$C_4$-alkyl or $C_1$-$C_4$-halogenalkyl having 1 to 5 halogen atoms, $R^{28}$ and $R^{29}$ independently of one another represent hydrogen, halogen, amino, nitro, $C_1$-$C_4$-alkyl or $C_1$-$C_4$-halogenalkyl having 1 to 5 halogen atoms, $R^{30}$ represents hydrogen, halogen, $C_1$-$C_4$-alkyl or $C_1$-$C_4$-halogenalkyl having 1 to 5 halogen atoms, $R^{31}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-halogenalkyl having 1 to 5 halogen atoms, $R^{32}$ represents halogen, $C_1$-$C_4$-alkyl or $C_1$-$C_4$-halogenalkyl having 1 to 5 halogen atoms, $R^{33}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-halogenalkyl having 1 to 5 halogen atoms, $R^{34}$ represents halogen, $C_1$-$C_4$-alkyl or $C_1$-$C_4$-halogenalkyl having 1 to 5 halogen atoms, $R^{35}$ represents halogen, $C_1$-$C_4$-alkyl or $C_1$-$C_4$-halogenalkyl having 1 to 5 halogen atoms, $R^{36}$ represents hydrogen or $C_1$-$C_4$-alkyl, $R^{37}$ represents halogen or $C_1$-$C_4$-alkyl, $R^{38}$ represents $C_1$-$C_4$-alkyl or $C_1$-$C_4$-halogenalkyl having 1 to 5 halogen atoms, $R^{39}$ represents hydrogen, halogen, $C_1$-$C_4$-alkyl or $C_1$-$C_4$-halogenalkyl having 1 to 5 halogen atoms, $R^{40}$ represents halogen, hydroxy, $C_1$-$C_4$-alkyl, $C_1$-$C_4$-alkoxy, $C_1$-$C_4$-alkylthio, $C_1$-$C_4$-halogenalkyl, $C_1$-$C_4$-halogenalkylthio or $C_1$-$C_4$-halogenalkoxy having in each case 1 to 5 halogen atoms, $R^{41}$ represents hydrogen, cyano, $C_1$-$C_4$-alkyl, $C_1$-$C_4$-halogenalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkylsulphonyl, di($C_1$-$C_4$-alkyl)aminosulphonyl, $C_1$-$C_6$-alkylcarbonyl or in each case optionally substituted phenylsulphonyl or benzoyl, $R^{42}$ represents hydrogen, halogen, $C_1$-$C_4$-alkyl or $C_1$-$C_4$-halogenalkyl having 1 to 5 halogen atoms, $R^{43}$ represents hydrogen, halogen, cyano, $C_1$-$C_4$-alkyl or $C_1$-$C_4$-halogenalkyl having 1 to 5 halogen atoms, $R^{44}$ represents hydrogen, halogen, $C_1$-$C_4$-alkyl or $C_1$-$C_4$-halogenalkyl having 1 to 5 halogen atoms, $R^{45}$ represents $C_1$-$C_4$-alkyl.

2. A process for preparing a carboxamide according to claim 1, comprising reacting a (a) carbonyl halides of the formula (II)

in which $X^1$ represents halogen or hydroxy with a cyclopropylamine of formula (III)

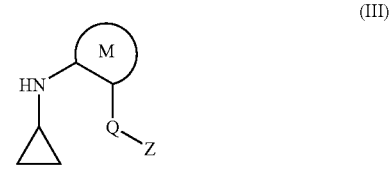

if appropriate in the presence of a coupling agent, if appropriate in the presence of an acid binder and if appropriate in the presence of a diluent.

3. A composition capable of controlling an unwanted microorganism, comprising at least one carboxamide according to claim 1, and an extender and/or surfactant.

4. A carboxamide according to claim 1 that is used for controlling an unwanted microorganism.

5. A method for controlling an unwanted microorganism, comprising applying a carboxamide according to claim 1 to the microorganism and/or a habitat thereof.

6. A process for preparing compositions for controlling unwanted microorganisms, characterized in that carboxamides of the formula (I) according to claim 1 are mixed with an extender and/or surfactant.

7. A method for treating seed comprising using a carboxamide of claim 1.

8. A method for treating a transgenic plant comprising using a carboxamide of claim 1.

9. A method for treating seed of a transgenic plant comprising using a carboxamide of claim 1.

* * * * *